United States Patent
Wiley et al.

(10) Patent No.: US 8,603,037 B1
(45) Date of Patent: Dec. 10, 2013

(54) INTRAVASCULAR NEEDLE AND CATHETER ASSEMBLY AND GRIP FOR THE SAME

(75) Inventors: Christopher W. Wiley, Grantham, NH (US); Michael Ewaschuk, Vershire, VT (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 0 days.

(21) Appl. No.: 13/442,344

(22) Filed: Apr. 9, 2012

Related U.S. Application Data

(60) Provisional application No. 61/473,974, filed on Apr. 11, 2011.

(51) Int. Cl.
*A61M 5/178* (2006.01)

(52) U.S. Cl.
USPC ................. 604/165.02; 604/168.01

(58) Field of Classification Search
USPC .................................... 604/165.02
See application file for complete search history.

(56) References Cited

U.S. PATENT DOCUMENTS

| | | |
|---|---|---|
| 4,645,491 A | 2/1987 | Evans |
| 4,699,612 A | 10/1987 | Hamacher |
| 4,808,158 A | 2/1989 | Kreuzer et al. |
| 5,100,390 A | 3/1992 | Lubeck et al. |
| 5,290,246 A | 3/1994 | Yamamoto et al. |
| 5,368,573 A | 11/1994 | Andrew |
| 5,407,441 A | 4/1995 | Greenbaum |
| 5,478,328 A | 12/1995 | Silverman et al. |
| 5,538,009 A | 7/1996 | Byrne et al. |
| 5,601,559 A | 2/1997 | Melker et al. |
| 5,649,911 A | 7/1997 | Trerotola |
| 5,843,048 A | 12/1998 | Gross |
| 5,868,699 A | 2/1999 | Woodruff et al. |
| 5,951,528 A | 9/1999 | Parkin |
| 6,273,877 B1 | 8/2001 | West et al. |
| 6,554,809 B2 | 4/2003 | Aves |
| 6,702,790 B1 | 3/2004 | Ross et al. |
| 7,002,098 B2 | 2/2006 | Adams |
| D561,338 S | 2/2008 | Blanco |
| 2005/0165355 A1* | 7/2005 | Fitzgerald ................ 604/164.08 |
| 2010/0137804 A1 | 6/2010 | Wiley |
| 2012/0101440 A1* | 4/2012 | Kamen et al. ............ 604/164.08 |

FOREIGN PATENT DOCUMENTS

| | | |
|---|---|---|
| DE | 3643235 C1 | 11/1987 |
| DE | 9400470 | 3/1994 |
| DE | 19512607 A1 | 10/1996 |
| DE | 29807150 | 8/1998 |
| DE | 10300452 A1 | 10/2003 |
| EP | 0824932 A2 | 2/1998 |
| WO | 03089035 A1 | 10/2003 |

* cited by examiner

*Primary Examiner* — Jason Flick
(74) *Attorney, Agent, or Firm* — Loginov & Associates, PLLC; William A. Loginov; Keri E. Sicard

(57) ABSTRACT

A needle, catheter, and housing assembly is provided. The assembly includes a slider portion that slides relative to the housing. The slider portion can be actuated by a caregiver/operator such that a catheter can be threaded into a patient with simple movement of the operator's thumb or other finger. The assembly also includes an improved flash chamber. The flash chamber utilizes capillary action and/or a visible portal area to provide a caregiver/operator with more immediate information as to whether the needle has been inserted in the vein or artery.

20 Claims, 29 Drawing Sheets

INTRAVASCULAR NEEDLE AND CATHETER ASSEMBLY AND GRIP FOR THE SAME

RELATED APPLICATIONS

This application claims the benefit of U.S. Provisional Application Ser. No. 61/473,974, filed Apr. 11, 2011, entitled INTRAVASCULAR NEEDLE AND CATHETER ASSEMBLY AND GRIP FOR THE SAME, the entire disclosure of which is herein incorporated by reference.

FIELD OF THE INVENTION

The present invention relates to a needle, catheter, and housing assembly for intravascular needles and arterial catheters.

BACKGROUND OF THE INVENTION

One of the most commonly performed invasive procedures in modern medicine is the insertion of an intravenous ("IV") or arterial catheter. Unfortunately, such procedures can require substantial skill for success, and even experienced and skilled practitioners have significant failure rates. This results in considerable pain and anxiety for the patient who may have to endure multiple attempts. Patients will often vividly recall having suffered failed IV or arterial insertions in the past.

Many failures can be attributed to a single point in this multi-step procedure: the attempt to thread the catheter after the vessel has been punctured by the needle and flashback of blood has occurred. Beginners often fail to appreciate that when flashback occurs, the needle tip (and orifice) are in the vein or artery, but the catheter tip may have not yet entered the vessel. They attempt to thread the catheter immediately upon flashback and thereby "blow" the insertion, because the catheter tip pushes the pliant vessel off the needle. Experienced practitioners, on the other hand, realize that following flashback, the entire needle/catheter assembly must be inserted an additional 2 mm or so before catheter threading is attempted. Yet the practitioner must be cautious to avoid over-insertion. Over-insertion will cause the sharp tip of the beveled needle to penetrate the "back" distal wall of the vessel, thereby resulting in failure and a painful hematoma. Accordingly, IV needle insertion is a precise, and often difficult, procedure for practitioners to perform.

By way of further illustration of this undesirable outcome, reference is made to FIG. 1, which depicts a typical needle and catheter arrangement 100 according to the prior art. The arrangement 100 includes a hollow metallic (typically surgical stainless steel) insertion needle 110 with a lumen 112 of appropriate size/diameter for the blood vessel 120 into which it is inserted (For example, needle sizes 14 gauge (G), 16 G, 18 G, 20 G, 22 G or 24 G). The distal end of the needle includes a conventional sharp, beveled, chisel-like tip 114 with an open orifice 116 that extends proximally into the lumen directly from the angled cylindrical orifice edge. This tip includes a distal point 118 that is quite sharp and enables piercing of the skin layer 122 and vascular wall 124 as shown with minimal discomfort for the patient. Overlying the needle 110, proximal of the tip 114 is a closely conforming catheter 130 constructed from a biocompatible polymer of conventional design. The distal end 132 of the catheter ends proximally of the angled tip 114, forming a small-diameter step that normally passes into the puncture hole created by the tip 114. The proximal end of the arrangement 110 typically includes an assembly with a distal portion that defines a fitting 142 interconnected with the catheter 130 and a proximal portion 144 that is interconnected with the needle. The two portions 142 and 144 can be withdrawn axially from each other so as to withdraw the needle 110 proximally from within the catheter lumen, while maintaining or advancing the catheter 130 distally with respect to the vessel 120 so as to thread and implant the catheter fully into the vessel.

As shown in FIG. 1, the needle tip 114 has been inserted by the clinician into the vessel 120 and the now-open path between a distal-most portion 150 of the tip orifice 116 and the bloodstream causes the flashback of blood through the needle lumen 112, which is visible in a flash chamber 160 at the proximal end. However no portion (or substantially no portion) of the catheter's distal end 132 has entered the vessel 120. Thus, an inexperienced or inattentive clinician may attempt to thread the catheter immediately upon such flashback. This premature threading generally causes the clinician to blow the insertion, because the catheter tip 132 pushes the pliant vessel 120 away from, and off of, the needle as the catheter is driven distally in an attempt to implant it in the vessel.

As set forth above, more experienced practitioners are aware that, following flashback, the entire needle/catheter arrangement 100 should be inserted an additional distance before catheter threading is attempted. Unfortunately, as further illustrated in FIG. 2, the sharp, beveled point 118 on the distal tip of the needle 110 may penetrate the distal back wall 210 of the vessel 120 during this additional insertion. This may result in a failed insertion and a painful hematoma.

SUMMARY OF THE INVENTION

This invention overcomes disadvantages of the prior art by providing an illustrative needle, catheter, and housing assembly for an IV or arterial catheter. This needle, catheter, and housing assembly can include a slider portion that slides relative to the housing/grip portion. The slider portion can be actuated by a caregiver/operator such that a catheter can be threaded into a patient with a straightforward movement of the operator's finger. As the slider is slide distally, the needle shaft is also covered so as to protect and shroud it.

An illustrative flash chamber can be provided. The flash chamber can utilize capillary action and a visible portal area to more rapidly or quickly provide a caregiver/operator with information as to whether the needle has been inserted in the vein or artery. The portal area can illustratively define a two-piece construction with a transparent window and underlying base each having confronting walls that form a capillary chamber therebetween. These components can be joined together in a sealed arrangement using a variety of novel and/or conventional techniques/structures.

Additional features of the disclosure will become apparent to those skilled in the art upon consideration of the following detailed description of illustrative embodiments exemplifying the best mode of carrying out the invention as presently perceived.

In an illustrative embodiment the catheter and insertion needle assembly, includes an insertion needle and a catheter forming a sleeve that overlies at least a portion of the insertion needle. A housing is coupled to the insertion needle and the catheter. The insertion needle and catheter are slidably mounted to the housing to permit movement of the insertion needle relative to the catheter, and to permit approximately coaxial movement of the insertion needle and the catheter relative to the housing. Illustratively, the housing comprises a chamber having a capillary channel for more quickly receiving blood from a subject so as to indicate flashback when the needle is fully seated in the blood vessel and ready for threading of the catheter thereover. Illustratively, the housing includes a slider that enables the insertion needle and the catheter to slide relative to each other between position in which the catheter is remote from a tip of the insertion needle and a position in which the catheter covers the insertion needle. The housing can also include a slider that enables the insertion needle and the catheter to slide relative to each other between position in which the catheter is remote form a tip of the insertion needle and a position in which the catheter covers the insertion needle. The slider furthermore covers and shrouds the needle to avoid accidental needle-sticks when the slider is moved fully distally. Illustratively, the capillary channel comprises at least one capillary passage disposed between an outer wall of a bottom and an inner wall of a transparent top cover sandwiched together in a sealed relationship. The inner wall and the outer wall can thereby define one of (a) confronting polygonal surfaces, (b) alternating semicircular surfaces, (c) confronting concentric, spaced-apart semicircular (or otherwise curvilinear) surfaces (d) confronting planar surfaces (e) confronting non-concentric, semi-circular (or otherwise curvilinear) surfaces. The top cover can be attached to the bottom by interengaging formations, such as nubs, detents, shoulders, and the like. The needle tip can illustratively include a curved heel to reduce the chance of penetrating the opposite wall of a blood vessel and a side port that is arranged on a sharp (typically chisel point of the needle) to ensure flashback occurs after the needle is fully seated into the blood vessel.

BRIEF DESCRIPTION OF THE DRAWINGS

The invention description below refers to the accompanying drawings, of which.

DETAILED DESCRIPTION

Figure 1:
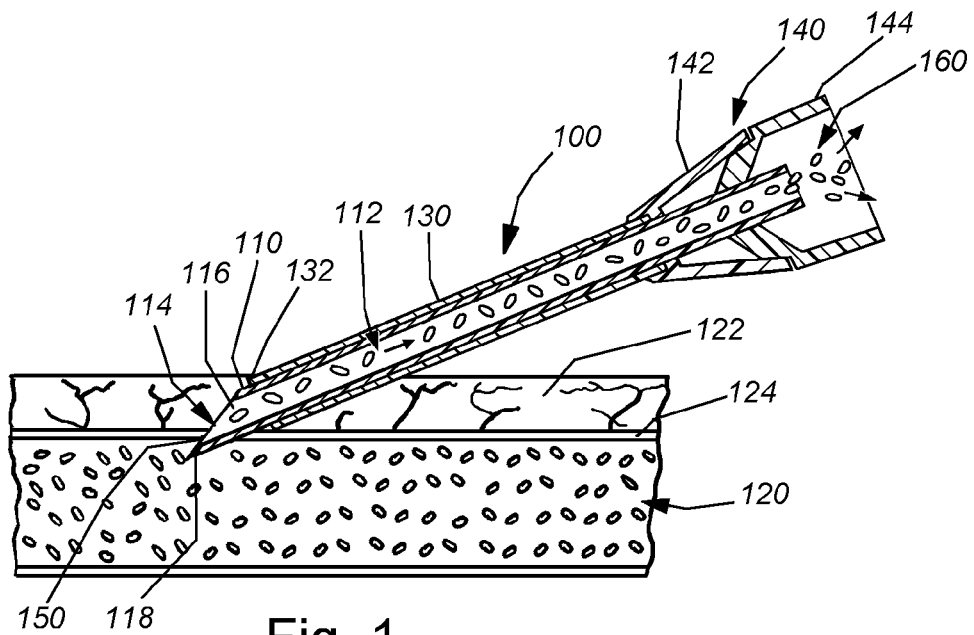
FIG. 1 is a front elevation view of a prior art needle being inserted into an exemplary vein.
Figure 2:
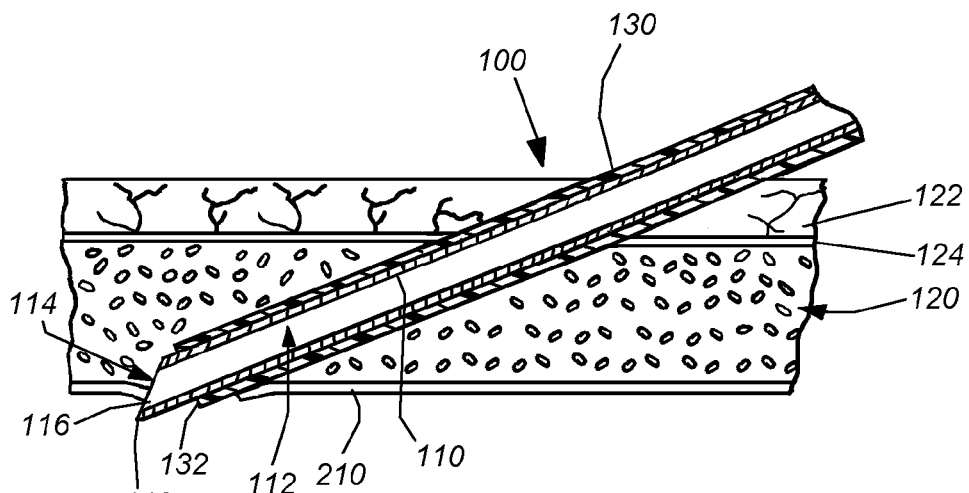
FIG. 2 is a front elevation view of the prior art needle of FIG. 1 being inserted into an exemplary vein to a point where it punctures a distal wall of the vein.
Figure 3:
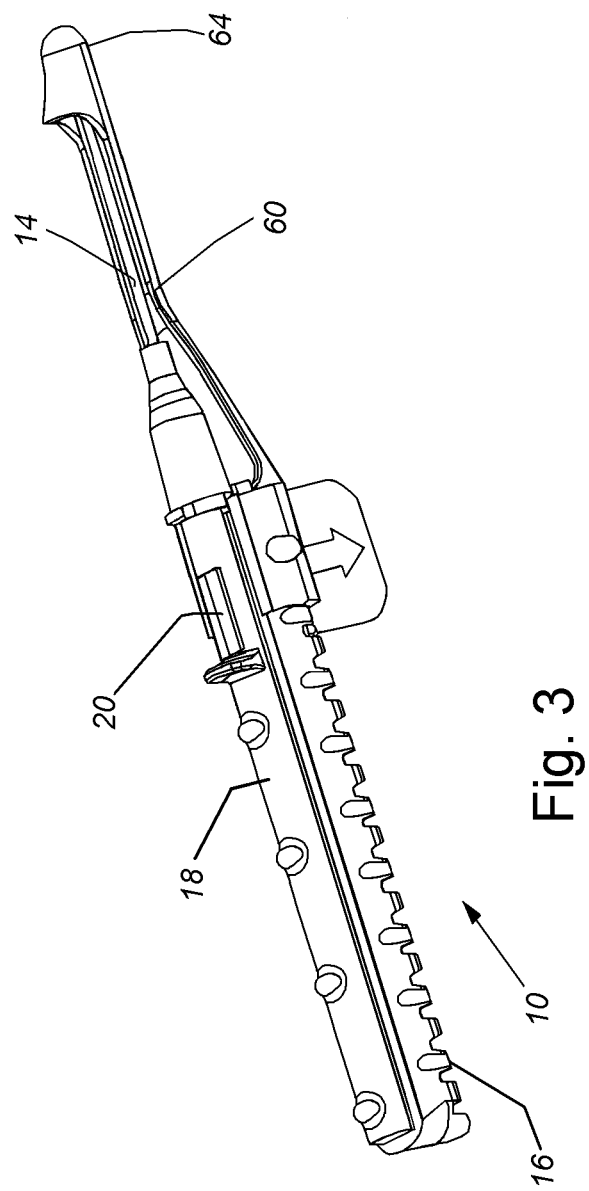
FIG. 3 is a perspective view of an assembly according to an illustrative embodiment.
Figure 4:
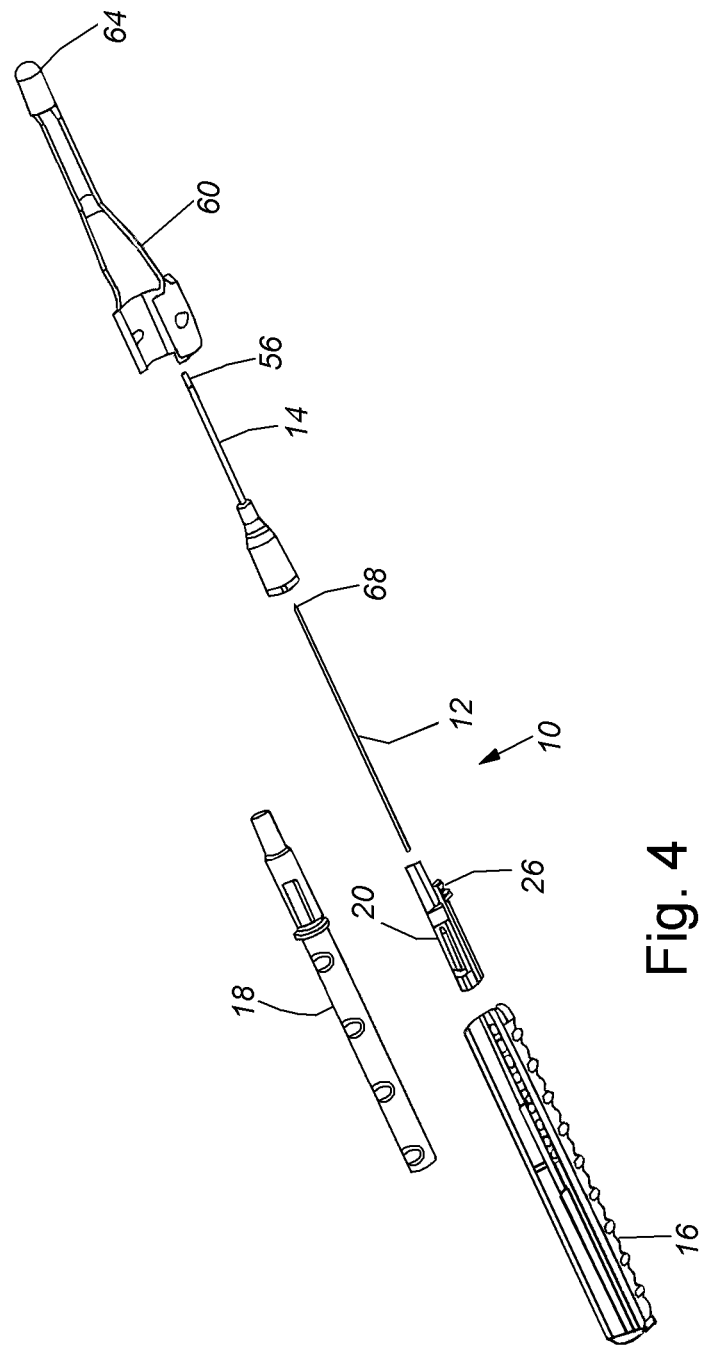
FIG. 4 is an exploded view of the assembly of FIG. 3.

One embodiment of the present disclosure is shown in FIGS. 3-16, in the form of an assembly 10. In an illustrative embodiment as shown, assembly 10 includes an insertion needle 12, a catheter 14 that forms a sleeve that overlies at least a portion of needle 12, and a housing 16 configured to be held by an operator. The assembly 10 also includes a sheath 60 that attaches to the housing 16. A distal end 64 of the sheath 60 overlies the tip 68 of the needle 12 and distal end 56 of the catheter 14 when, for example, the apparatus 10 is not in use (e.g., when first removed from its packaging). As shown in the exploded view in FIG. 4, catheter 14 is coupled to slider 18, and can slidably move over needle 12 in conjunction with slider 18. Housing 16 is illustratively configured to couple to needle 12 via flash chamber 20. As shown in FIGS. 3-4, flash chamber 20 includes an alignment portion 26 for aligning needle 12 with catheter 14 (via hub 52), as discussed in detail below.

Figure 5:
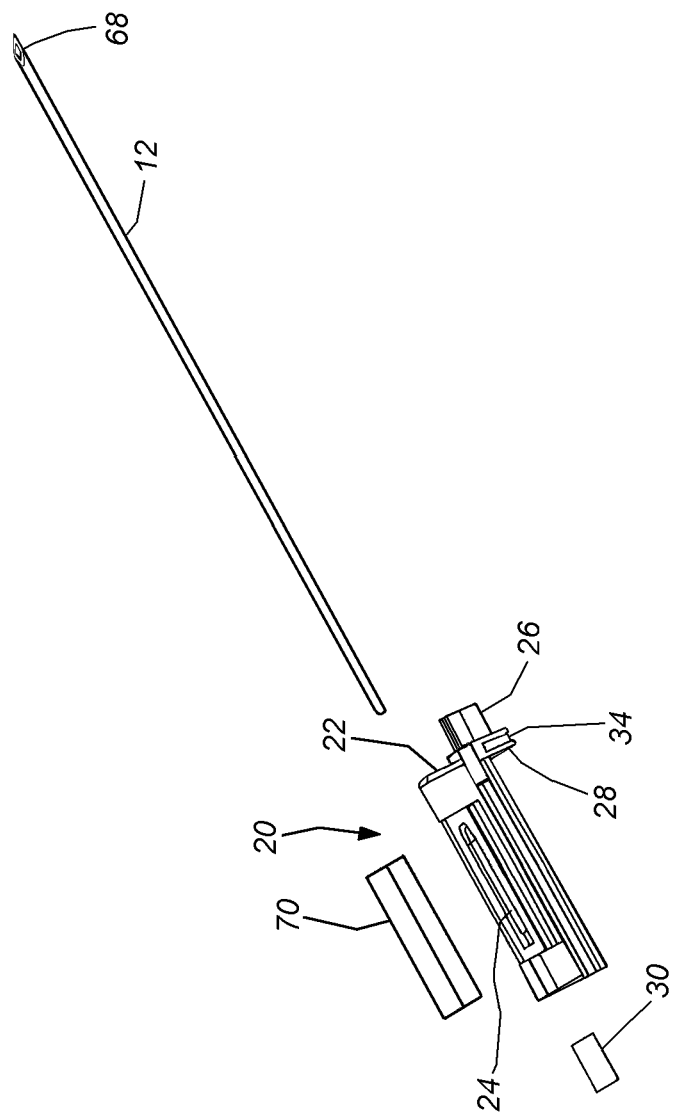
FIG. 5 is an exploded view of the needle and flash chamber of the illustrative embodiment.

FIG. 5 shows an enlarged view of flash chamber 20. In the illustrative embodiment, flash chamber 20 is configured so as to provide a needle receiving portion 22, a chamber portion 24, and an alignment portion 26. Alignment portion 26 is illustratively a tab that is configured to engage a slot in hub 52, as shown assembled in FIGS. 11 and 14. In the illustrative embodiment, a protrusion 28 supports alignment portion 26 and carries ridges 34, discussed below.

Chamber portion 24 of the flash chamber 20 is shown adjacent to sealing element 30. Sealing element 30 is contemplated to be a material that allows for the passage of air, but resists the passage of a fluid such as blood. For example, sealing element 30 may be formed of a tightly woven cotton or similar natural and/or synthetic material in an appropriate matrix or structure to provide pores/microchannels of a desired size. In the alternative, a vent channel can be provided within flash chamber 20.

According to an illustrative embodiment, the flash chamber 20 also includes a cover 70 (see inter alia FIG. 5). The combination of the chamber portion 24, cover 70 and sealing element 30 provide the capillary channel of the flash chamber 20. The combination functions in part to create a capillary effect within the flash chamber 20. By way of further background, capillary action is the ability of liquid to flow against gravity where liquid spontaneously rises in a narrow space such as a thin tube or channel, or in porous materials such as paper. This effect can cause liquids to flow against the force of gravity. It occurs because of inter-molecular attractive forces between the liquid and surrounding solid surfaces of the tube or channel. If the diameter of the tube or cross-sectional area of the channel is sufficiently small, then the combination of surface tension (which is caused by cohesion within the liquid) and forces of adhesion between the liquid and solids surfaces of the tube or channel act to move the liquid. The spaced relationship between the cover 70 and the chamber portion 24 contributes to the capillary effect by conserving the amount of bodily fluid that must be drawn into chamber portion 24. Moreover, the space between the cover 70 and walls of chamber portion 24 can be minimized so as to increase the capillary action. In the illustrative embodiment, as bodily fluid is drawn into chamber portion 24, the capillary effect causes bodily fluid to move along a path spanning the length of the interior volume of the flash chamber 20. Such a path simultaneously spreads bodily fluid (i.e., blood) over the visible portal area 33 (shown in FIGS. 11 and 12). Accordingly, a caregiver can more quickly/immediately visualize when bodily fluid has entered into flash chamber 20. This quick-drawing action can provide, for example, much (or significantly) faster viewing of the bodily fluid by an operator while drawing less bodily fluid. In another embodiment, chamber portion 24 can be exchanged for two closely positioned walls that define a relatively small space therebetween. Such a small space between two walls will similarly create the capillary action discussed herein.

Figure 6:
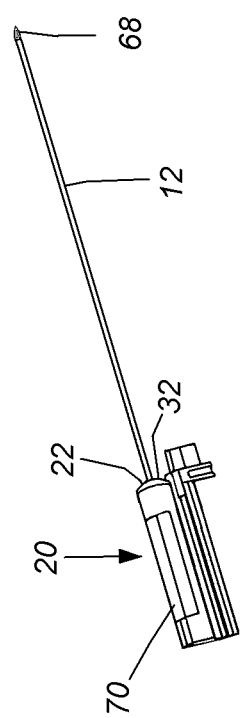
FIG. 6 is a perspective view of the needle coupled to the flash chamber.
Figure 7:
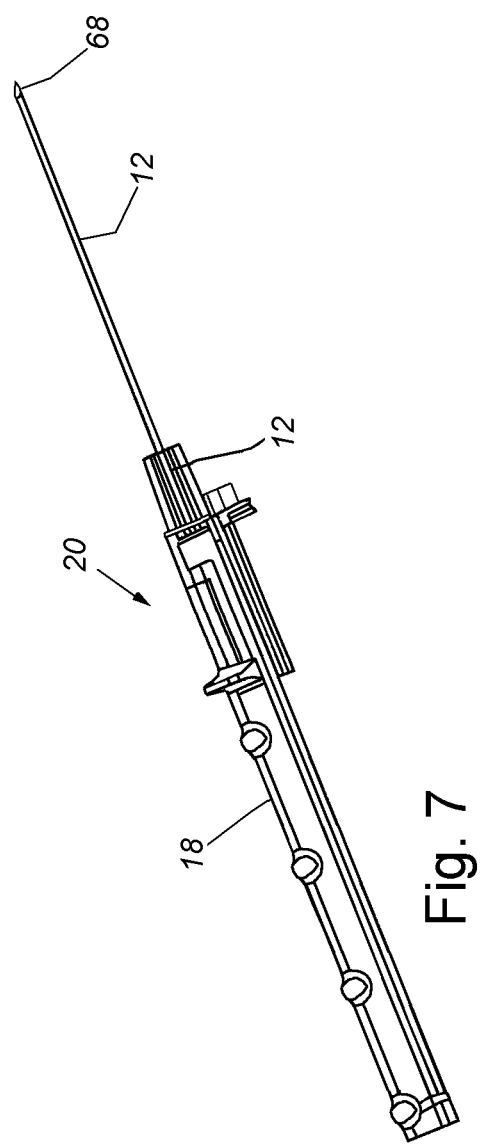
FIG. 7 is a perspective view of the needle and flash chamber positioned inside the slider.

With reference to FIG. 6, a needle receiving portion 22 of flash chamber 20 is shown coupled to a proximal end 32 of needle 12. FIG. 7 shows needle 12 and flash chamber 20 positioned within slider 18. In the illustrative embodiment, needle 12 and flash chamber 20 are slidably movable within slider 18.

Figure 8:
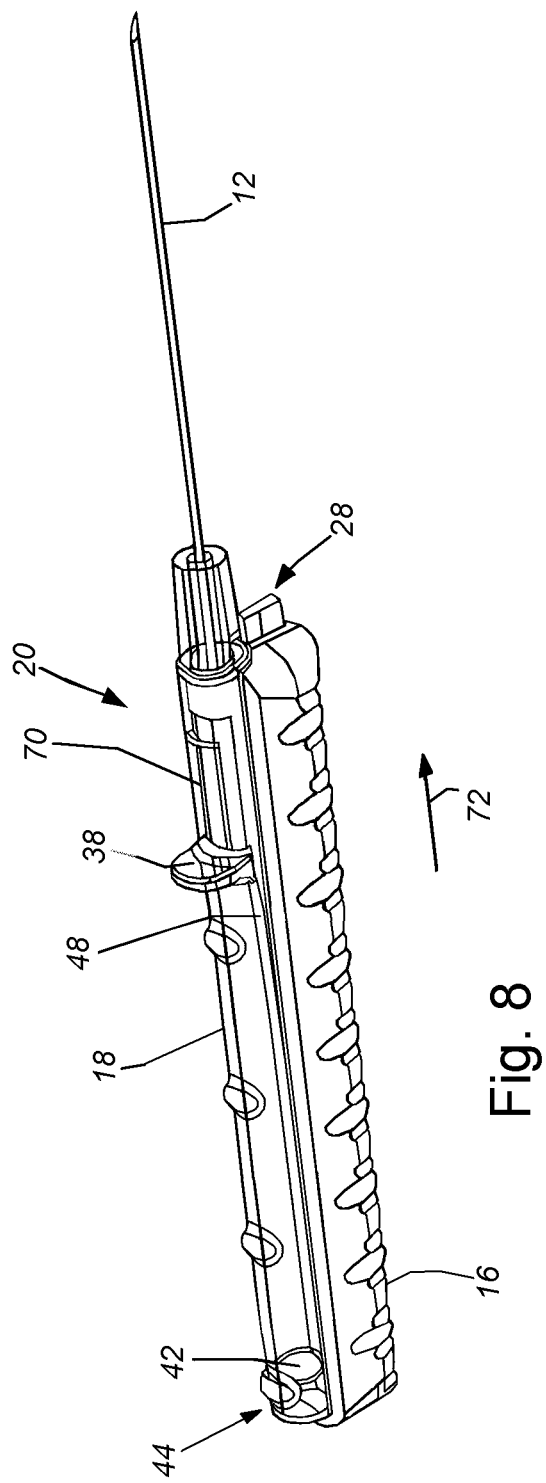
FIG. 8 is a perspective view of the needle, flash chamber, slider, and housing prior to final assembly.

FIG. 8 shows the slider 18 (shown in phantom), needle 12, and flash chamber 20 of FIG. 6 coupled with housing 16. As shown in FIG. 8, flash chamber 20 has at least one ridge 34 formed in protrusion 28. Such at least one ridge 34 is illustratively configured to engage with at least one indentation 36, formed in housing 16. In the illustrated embodiment, ridge 34 and indentation 36 interlock such that flash chamber, and therefore needle 12, are attached to housing 16 and move with housing 16.

Figure 9:
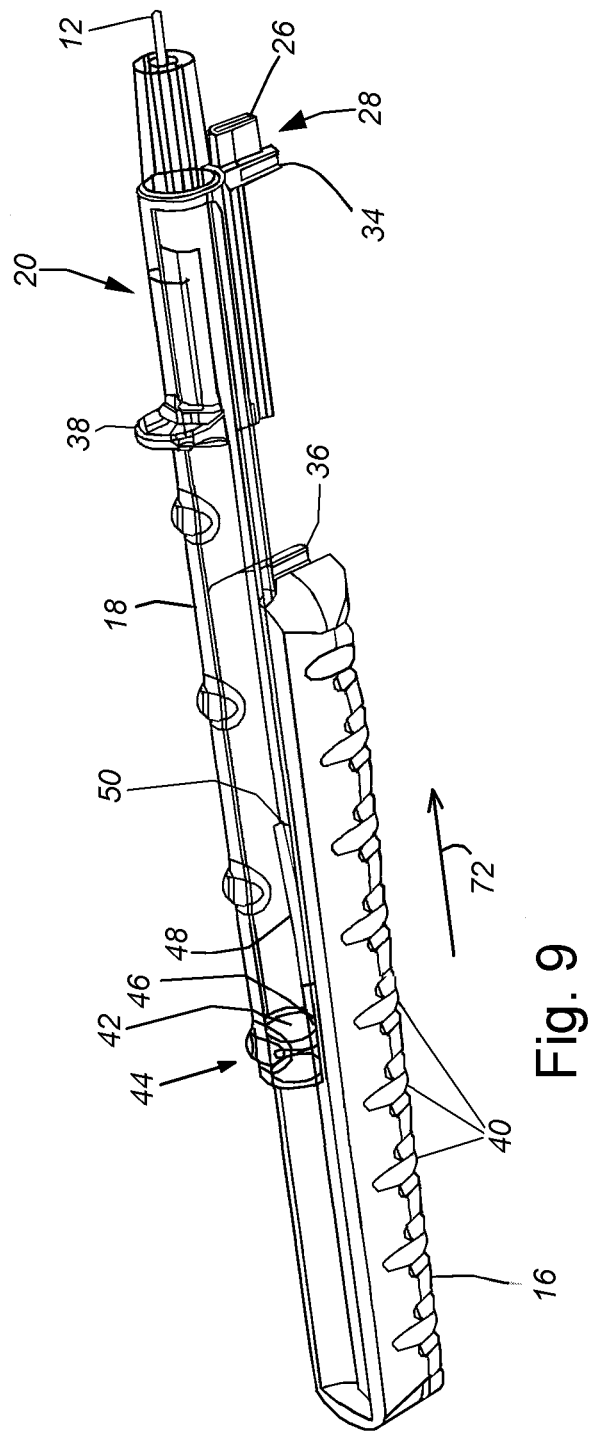
FIG. 9 is another perspective view of the needle, flash chamber, slider, and housing prior to final assembly.

FIGS. 8-9 show relative movement of slider 18 in relation to housing 16 along a distally oriented "advance" direction, as indicated by arrow 72. Slider 18 illustratively includes a raised portion 38 that can be urged by, for example, an operator's thumb or other finger. Likewise, housing 16 can have contours 40 that can be gripped by an operator's fingers or palm. In the illustrative embodiment, slider 18 can be urged relative to housing 16 by an operator (i.e. a caregiver), thereby causing catheter 14 (which is coupled to slider 18, as shown in FIG. 3) to slide along the length of needle 12.

Slider lock 42 is positioned near a first end 44 of slider 18. As slider 18 is urged (by an operator) to move relative to housing 16, groove 46 is caused to move along ramp 48, thereby depressing ramp 48 as first end 44 of slider approaches flash chamber 20. Once slider lock 42 passes over tip 50 of ramp 48, ramp 48 returns back to its original, raised position, thereby locking slider lock in place relative to housing 16 to prevent movement along the proximally oriented "retract" direction opposite the advance direction that is indicated arrow 72).

Figure 10:
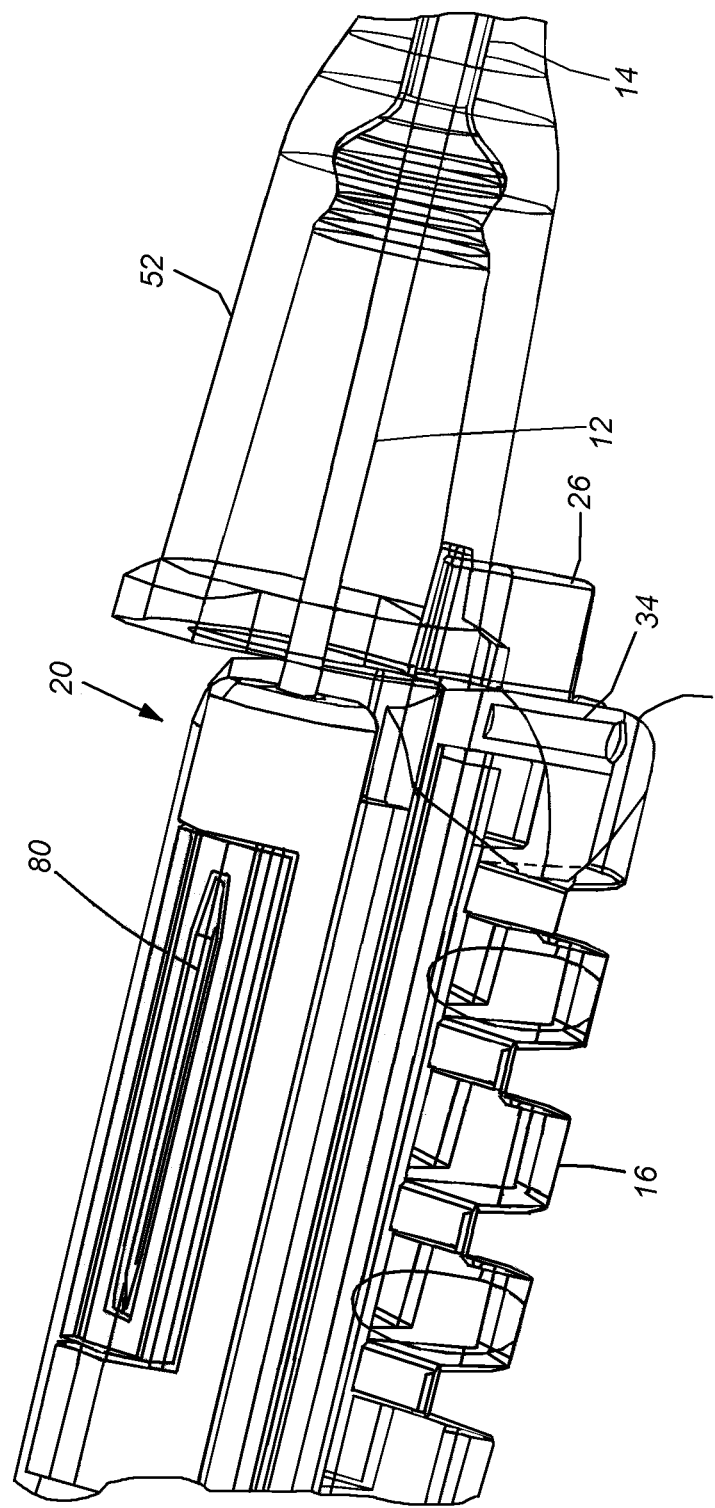
FIG. 10 is an enlarged view of the capillary portion of the flash chamber.

FIG. 10 is an enlarged view of housing 16 where it engages with capillary channel 80 of flash chamber 20. Cover 70 of the flash chamber is illustrated in phantom to provide visibility of channel 80. As discussed above, ridge 34 is shown engaged with indentation 36 of housing 16, thereby fixing flash chamber 20 relative to housing 16. Moreover, alignment portion 26 is illustratively shown extending into a slot formed in hub 52, such that hub 52 (and therefore catheter 14) can be aligned relative to the rest of assembly 10.

Figure 11:
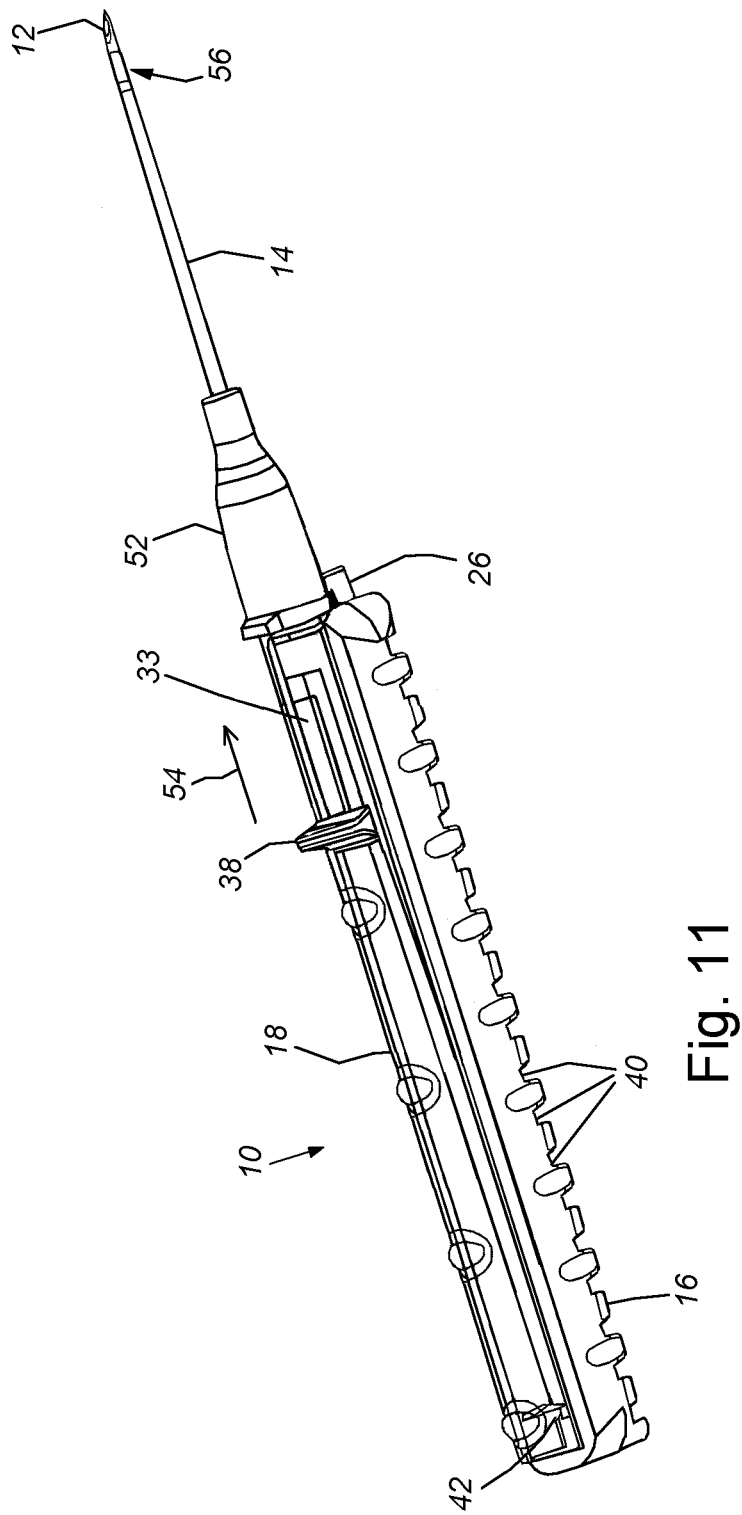
FIG. 11 is a top perspective view of the assembly.

A fully assembled, and ready for deployment, assembly 10 is shown in FIG. 11. As shown in FIG. 10, slider 18 is coupled to a hub 52. Hub 52 is likewise coupled to catheter 14. Accordingly, when an operator urges slider 18 via raised portion 38 in the distally oriented direction indicated by arrow 54, hub 52 and catheter 14 are urged to move with slider 18. Hub 52 travels along alignment portion 26 for a short distance before it is free from alignment portion 26. It is contemplated that such alignment might be necessary when, for example, catheter 14 is configured to have a non-uniform distal end 56. As discussed below, in one embodiment, catheter 14 can be configured to be aligned with needle 12.

As slider 18 moves relative to housing 16, catheter 14 also moves relative to needle 12. In most medical settings, the optimal time for movement of slider 18 relative to housing 16 will be at the approximate time when needle 12 has pierced a vein or artery, and blood is visible in flash chamber 20. By moving slider 18 relative to housing 16, an operator causes catheter 14 to be threaded into the vein or artery, and meanwhile, needle 12 to be removed from the vein or artery.

In the illustrative embodiment, an operator is protected from accidental needle sticks by virtue of the design of the slider lock 42 and housing 16. When the operator urges slider 18 to move relative to housing 16, needle 12 is withdrawn into a recessed portion of slider 18. Once slider lock 42 has reached tip 50, slider 18 is locked into its position relative to housing 16. Accordingly, needle 12 is also locked into the recessed position of slider 18. In this position, accidental needle pricks can be avoided because needle 12 is safely tucked into slider 18.

Figure 12:
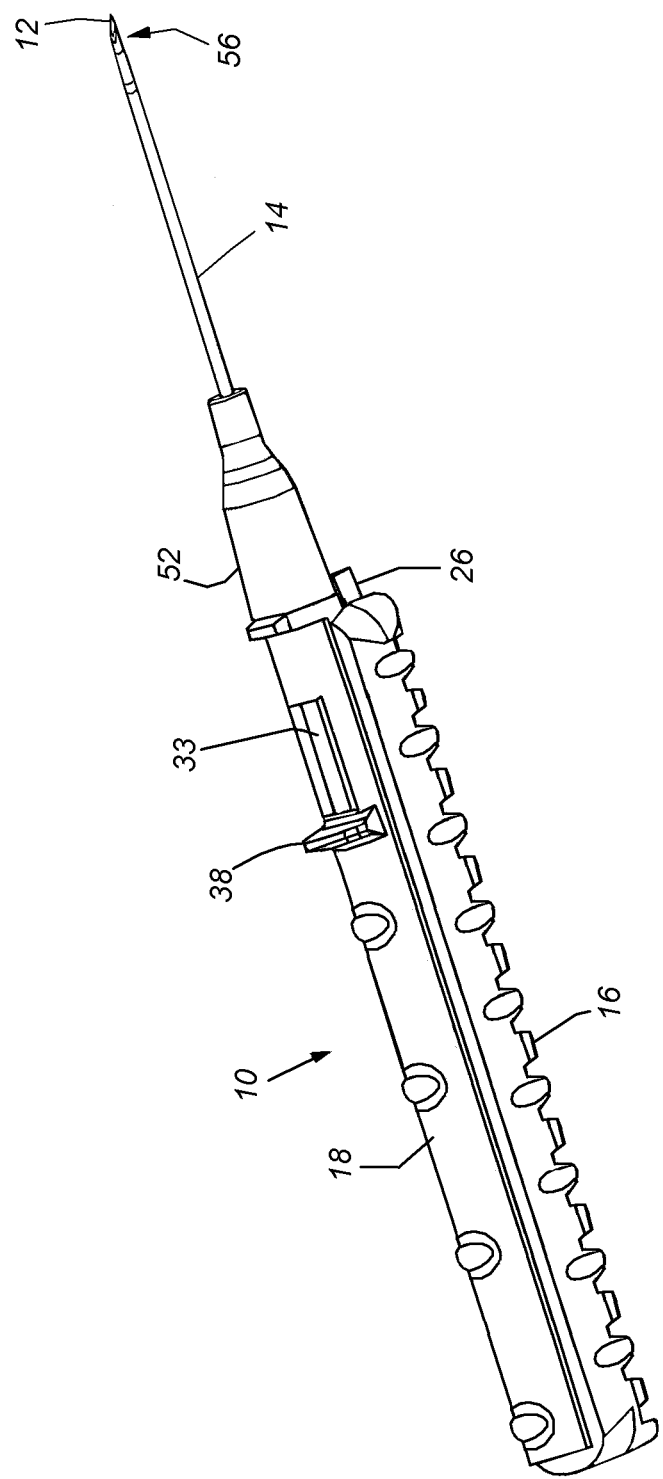
FIG. 12 is another top perspective view of the assembly shown in FIG. 11, prior to deployment.

According to the illustrated embodiment, an operator performs an IV or arterial catheter insertion in the following manner. An assembly 10 ready for use is shown in FIG. 12. An operator places the assembly 10 in his/her hand such that visible portal area 33 is facing upwardly, toward the operator. The operator's thumb or index finger can be placed on raised portion 38, and the operators remaining fingers grip the housing 16.

Needle 12 can have a tip such as that disclosed in U.S. Published Patent Application No. US 2010/0137804 A1, filed Nov. 23, 2009, entitled INTRAVASCULAR NEEDLE AND CATHETER ASSEMBLY, by Christopher W. Wiley, the teachings of which are incorporated herein by reference as useful background information. Moreover, catheter 14 can be formed at its distal end in a manner that aligns with needle 12, as disclosed in the referenced patent application. However, it should be understood that the inventions disclosed herein can be performed with any type of needle tip and catheter combination. In the above-incorporated published application, the needle tip generally defines: (a) a distal-most sharp point that is enclosed at a needle distal end; (b) a side port in fluid communication with a lumen of the needle shaft located on a first side adjacent to the shaft junction, and (c) an upwardly curved heel on the needle tip along a second side opposite the first side that extends from the junction to the distal-most sharp point and thereby locates the point adjacent to a longitudinal axis of the shaft.

Figure 12A:
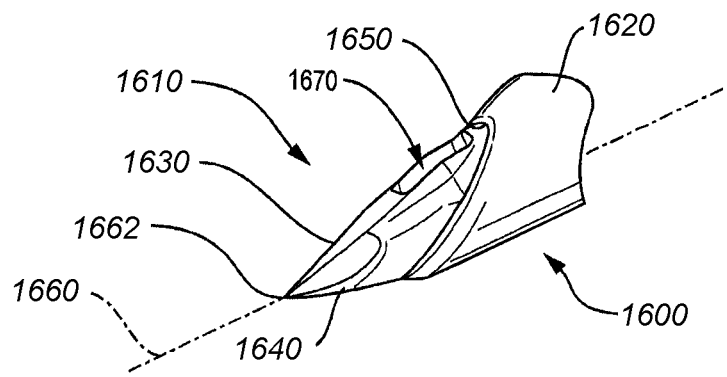
FIG. 12A is a partial perspective view of an illustrative needle assembly with overlying catheter and tip for use with the assembly according to various embodiments.
Figure 12B:
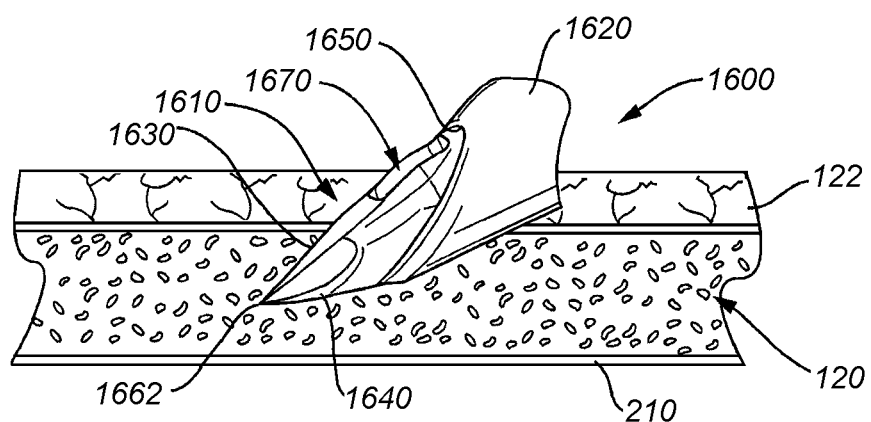
FIG. 12B is a perspective view showing, by way of example, the insertion of the needle of FIG. 12A into an exemplary vessel wherein flashback occurs only after the needle has been fully inserted into the vessel.
Figure 12C:
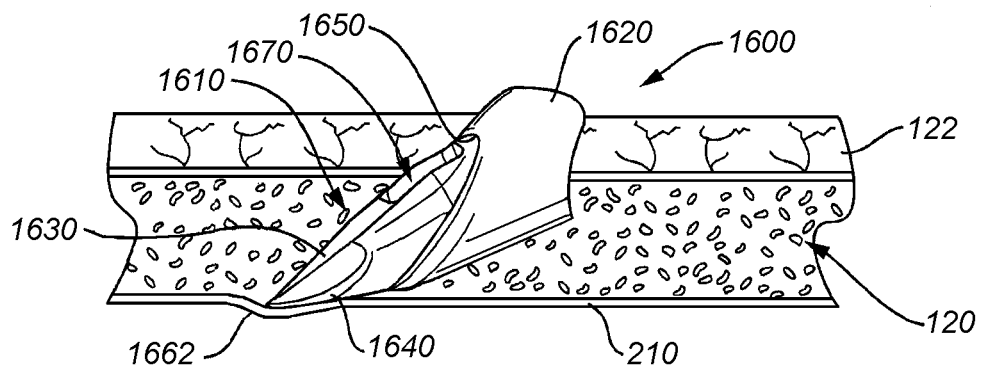
FIG. 12C is a perspective view showing the over-insertion of the needle of FIG. 12A into contact with the back wall of the vessel, and wherein the placement of the point and curved geometry of the second side of the tip reduces the risk of damage to the vessel.

With reference to FIGS. 12A, 12B and 12C, a needle assembly and needle tip according to an illustrative embodiment and as described in the above-incorporated published application is shown. This needle assembly and associated tip can be employed with the illustrative housing and slider in various embodiments. The depicted needle assembly 1600 includes a needle tip 1610 and a catheter 1620 overlying a shaft (not shown) of the needle 1600. It is noted that the needle tip 1610 and proximal needle shaft (not shown but underlying the catheter 1620) can be employed without a catheter in alternate embodiments, but are shown with an overlying catheter for descriptive purposes. The needle tip 1610 has a first (upper) side 1630 and an opposing (bottom) side 1640 defining a generally curved heel. The tip 1610 in this embodiment interconnects with a straight, cylindrical shaft section having the overlying catheter 1620 at a relatively circular junction 1650. The circular junction 1650 resides in a plane that is approximately perpendicular to the longitudinal (axis of elongation) 1660 taken long the center (cross sectional center/centroid) of the shaft 1620.

The tip 1610 includes a distal-most sharp enclosed point 1662 that resides approximately within the axis 1660 in this embodiment. It is contemplated, as with the other embodiments discussed herein, that in alternate embodiments the tip point 1662 may reside below or above the axis 1660. However, the point 1662 should be located so as to generate an upwardly curved surface 1640 of the tip 1610 that operates to reduce potential damage to the vascular wall. As shown in greater detail in FIG. 12C, the curved bottom surface 1640 of the tip 1610 reduces the risk of puncturing the vascular wall 210.

It is noted that the needle assembly 1600 is shown and described as including an overlying catheter in an illustrative embodiment of the invention. However, it is expressly contemplated that the needle structure itself is readily applicable to any medical treatment or method employing a needle free of an overlying catheter. The structure provides improved flashback readings to a user of the needle structure, desirable for not only catheter application, but any intravascular application, such as simple blood draws. In this manner, the needle is employed to determine that the orifice is fully within the vein, prior to drawing in the blood. The needle structure of this embodiment further reduces the risk of over-penetrating, and possibility of puncturing, a vessel wall, due to the curved heel of the needle. Where used in application as a "standalone" needle the proximal end can be fixedly or removably (using, for example a Luer fitting) attached to a syringe body or other fluid-draw/delivery device.

The needle assembly 1600 includes a side orifice or side port 1670 that is located on an upper side of the needle, opposite the curved heel, and proximally offset from the distal-most sharp enclosed point 1662. The side port 1670 is shown on a first (upper) side of the needle tip 1610, however it is expressly contemplated that the port 1670 can be displaced at a greater distance from the enclosed point 1662, on an upper side of the needle shaft (not shown), depending on the particular application for which the needle assembly 1600 is constructed and arranged. The port 1670 is in fluid communication with the blood vessel once inserted into a blood vessel, as shown and described with reference to FIGS. 12B and 12C.

FIGS. 12B and 12C detail an exemplary insertion procedure employing the needle arrangement according to an illustrative embodiment of this invention. In the depicted example the illustrative arrangement 1600 is employed. As shown in FIG. 12B, the needle assembly 1600, including the needle 1610 and overlying catheter 1620, has been inserted at an appropriate angle by a practitioner through the skin layer 122, into the exemplary blood vessel 120. As shown, the needle tip 1610 has just pierced the skin 122 and vascular wall and now resides fully in the vessel 120, in communication with the bloodstream. The distal end of the catheter 1620, which overlies the tip 1610 and the needle shaft is also fully within the vessel, although minimally. At this moment, the blood flows up the needle lumen, and flashback occurs at the capillary chamber, indicating the needle resides fully within the blood vessel.

As shown in FIG. 12C, where a practitioner inadvertently over-inserts (distally) the needle assembly 1600, the geometry of the heel, or second side of the tip 1640, and more-axial placement of the sharp enclosed point 1662 clearly reduce the risk of damage to the back wall 210 of the blood vessel 120. The back wall 210 is shown slightly depressed by the engagement with the tip 1610, and more particularly the heel 1640. However, the curved geometry of the heel blunts any damage to the wall and aids in redirecting the tip along the wall in an upwardly curving direction.

Figure 13:
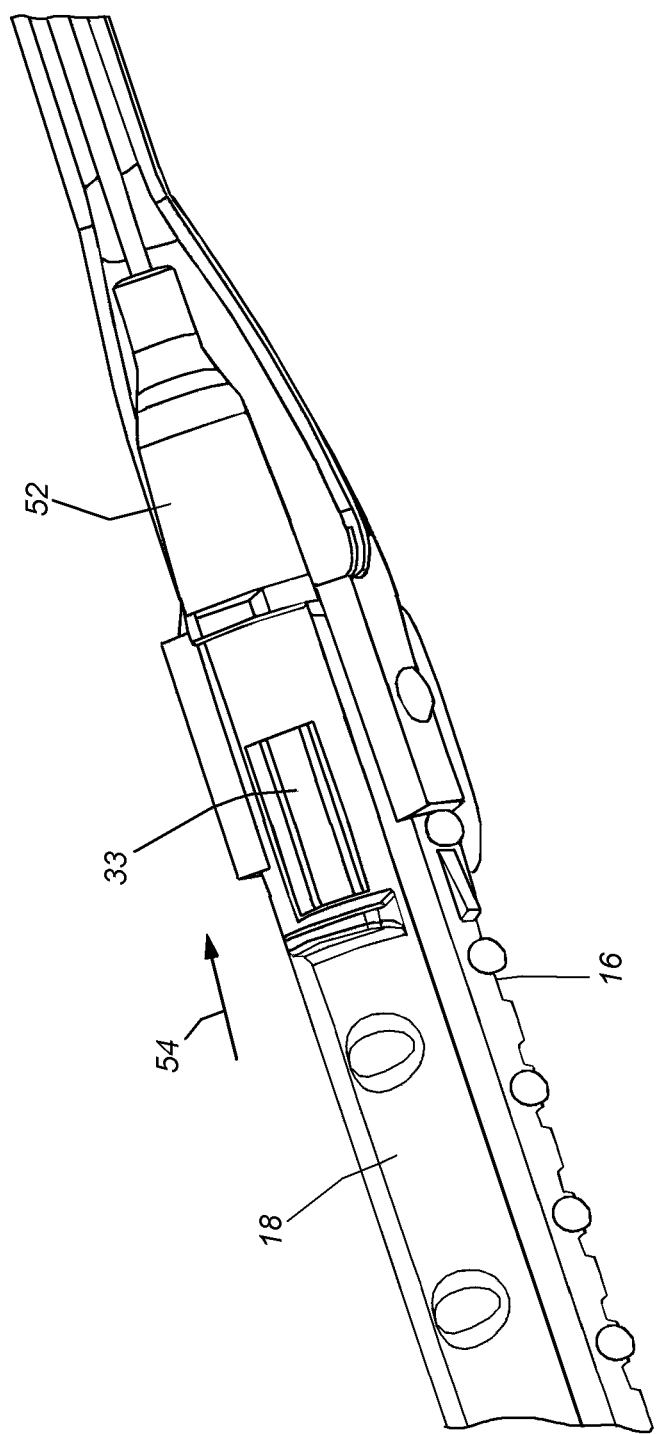
FIG. 13 is an enlarged view of the visible portal area visible through the slider surface.
Figure 14:
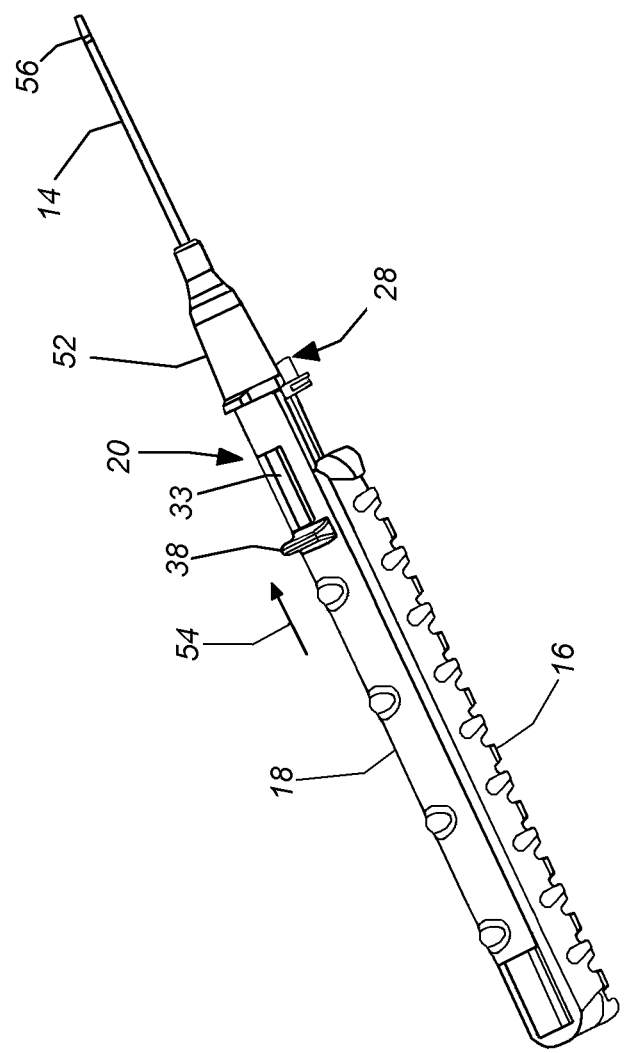
FIG. 14 is a perspective view of the assembly as it is being deployed.

As now shown in FIG. 13, after the needle has been inserted into a vein or artery, an operator can wish to closely watch visible portal area 33 for the earliest flashback of blood. When an operator is satisfied that the needle tip is properly inserted, the operator can urge raised portion 38 in the distally oriented direction indicated by arrow 54, and as shown in FIG. 14. In the position shown in FIG. 14, the catheter 14 has begun to thread off of needle 12.

Figure 16:
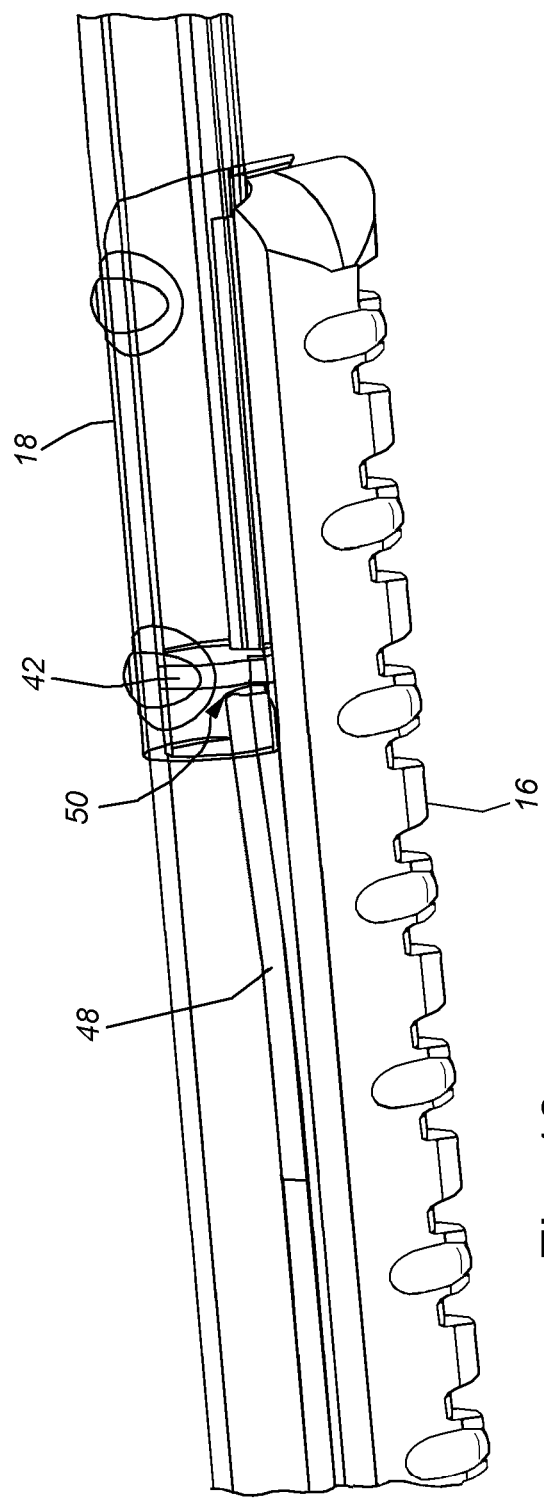
FIG. 16 is an enlarged view of the slider lock and ramp portions of the assembly.

When slider lock 42 has passed tip 50, as described above, the operator can feel, and typically hear, a tactile and/or audible "click" as slider lock 42 locks into place beyond tip 50, as shown in FIG. 16. At this time, an operator can remove hub 52 from the assembly 10 when desired thereby preventing blood spillage until infusion tubing or syringe is ready to be attached. Ideally, catheter 14 will be threaded, and properly in place in the patient's vein or artery by this time.

Figure 15:
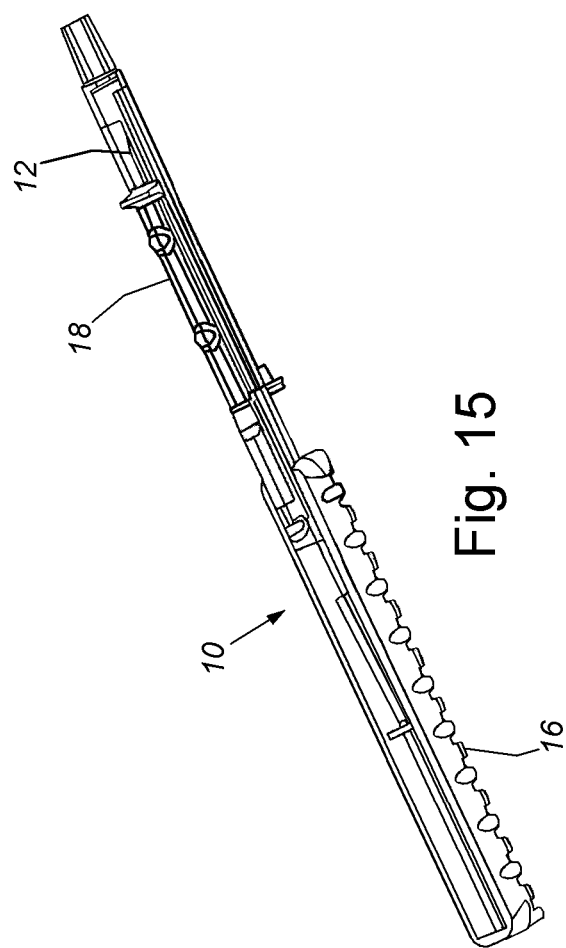
FIG. 15 is a perspective view of the assembly without the hub, after the slider has been deployed and the catheter has been detached after successful threading.

FIG. 15 illustrates an assembly 10 that has been deployed, wherein the slider 18 is locked in place relative to housing 16, and needle 12 is safely covered by slider 18. At this time, assembly 10 can be disposed of in a disposal container.

FIGS. 17A-17E are schematic cross-sectional illustrations of the capillary channel 80 according to illustrative embodiments of the above-described flash chamber 20. For the purpose of simplification, like reference numerals are used to describe similar functional/structural components for each version of the generalized flash chamber 20 to be described below, with the addition of a suffix A-E to delineate between each different, depicted construction. Each of the depicted, illustrative flash chambers 20 includes a chamber portion 24 (or base) and cover 70. The combination of the chamber portion 24 and cover 70 provide the capillary channel 80 of the flash chamber 20. The spaced relationship between chamber portion 24 and the cover 70 functions in part to create a capillary effect within the flash chamber 20. The various chamber constructions described herein are assembled according to a variety of techniques that form a fluid-tight connection between the portions. For example, the chamber can be formed from portions that are snap-fit, pressfit, slide-fit, adhered and/or welded (e.g. ultrasonically) together, or by another technique that is clear to those of skill in the art. Such techniques are described further below with respect to various illustrative embodiments.

Figure 17A:
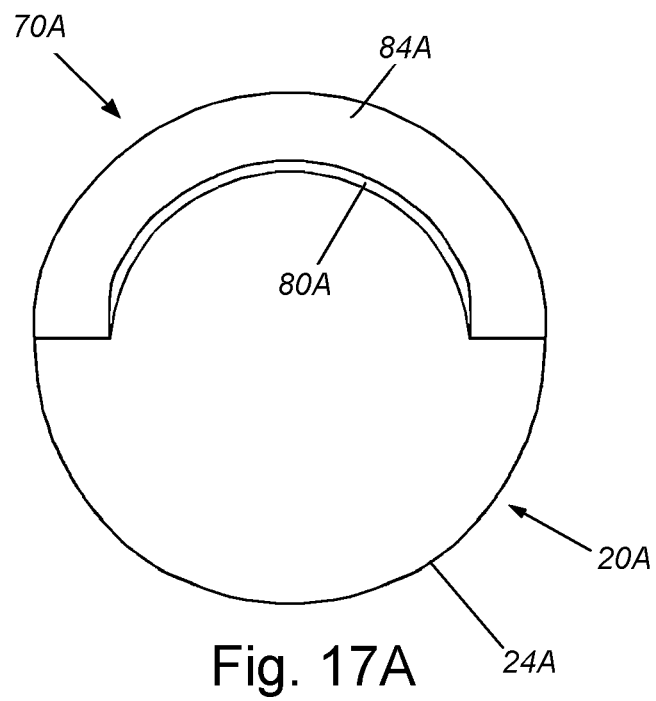
FIGS. 17A-17E are schematic cross-sectional illustrations of the capillary channel of various illustrative embodiments of a flash chamber of the assembly.

FIG. 17A illustrates a flash chamber 20A defined between two semi-circular, concentric walls that define a capillary channel 80A of substantially constant width (i.e. a substantially constant radial spacing about the arc of the chamber). The walls of this and other flash chambers described herein include a (typically opaque) outer wall of the bottom section (i.e. a housing portion) and an inside wall of a transparent or translucent cover. One or both walls can be shaped and/or formed to allow the passage of blood thereinto. More particularly, the relatively thin top half (cover 70A) of the flash chamber 20A allows the blood therein to be readily visible, and the semi-circular shape affords the operator a wide range of viewing angles from the top portion 84A of the flash chamber 20A.

Figure 17B:
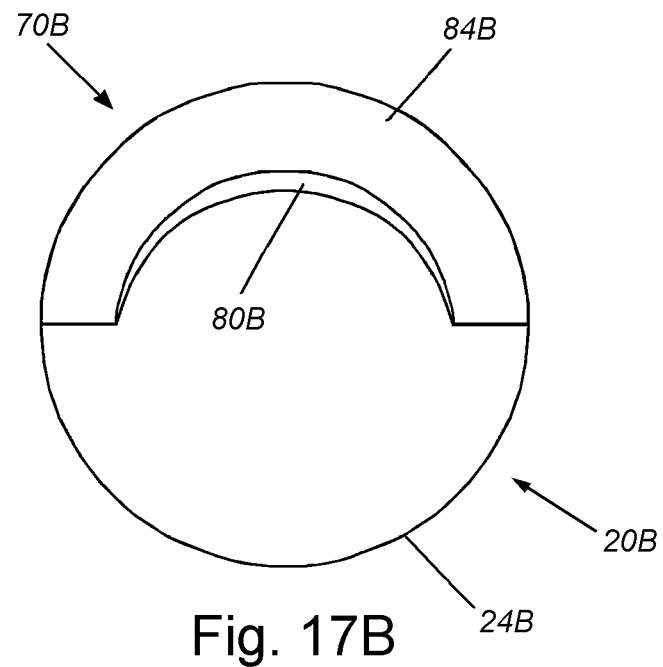

FIG. 17B illustrates a flash chamber 20B defined between two non-concentric semi-circular walls that likewise define a capillary channel 80B of varying thickness. Since the optimum thickness of the capillary channel varies depending on the characteristics of the blood contained therein, the use of a varying thickness for the channel advantageously provides that optimum thickness at one or more locations along the top portion 84B of the flash chamber 20B.

Figure 17C:
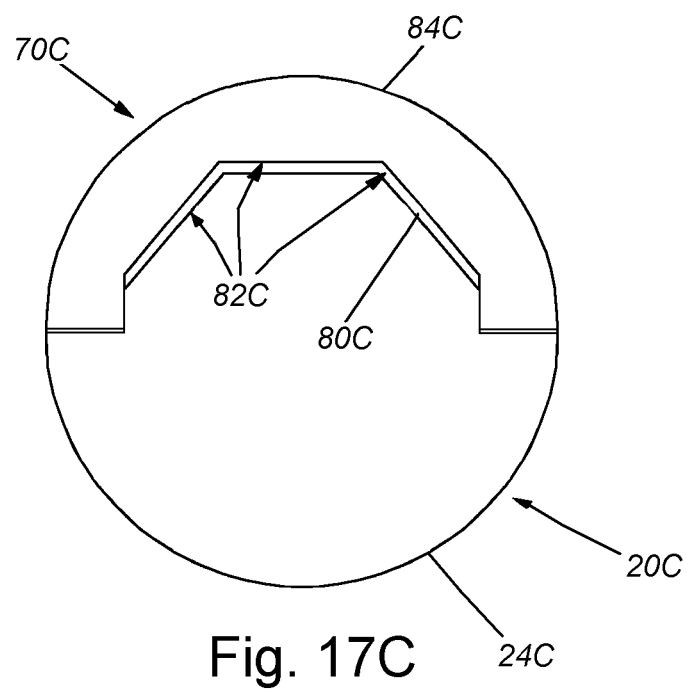
Figure 17D:
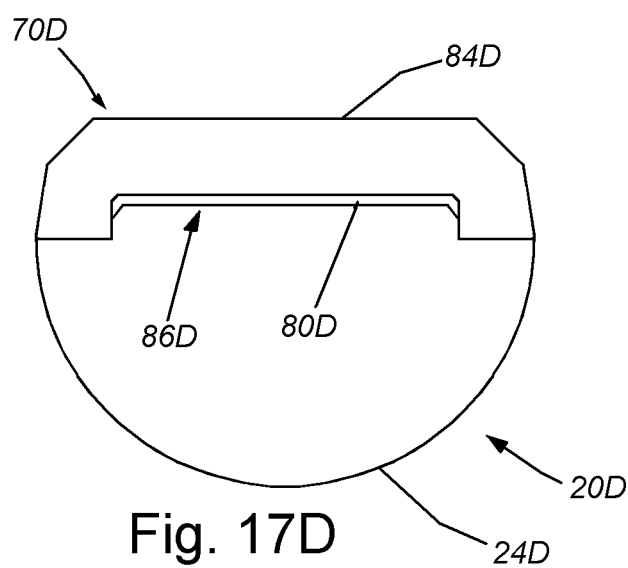

FIG. 17C illustrates a flash chamber 20C having a capillary channel 80C that includes three flat planar regions 82C formed by the combination of the chamber portion 24C and the cover 70C. This structure generally defines a "nested polygonal" wall structure in cross section. Alternatively, FIG. 17D illustrates a flash chamber 20D having a capillary channel 80D that is defined by a pair of spaced-apart confronting walls, each having a continuous planar shape so as to define a substantially constant-spacing/width region 86D. This region is constructed from a combination of the depicted chamber portion 24D and the cover 70D. In an alternate embodiment, the confronting, planar walls can be oriented at a non-parallel angle (with respect to each other) to achieve some of the advantages shown in the embodiment of FIG. 17B. Likewise, the confronting planar walls of one or more facets of the nested polygonal chamber in FIG. 17C can be non-parallel.

Figure 17E:
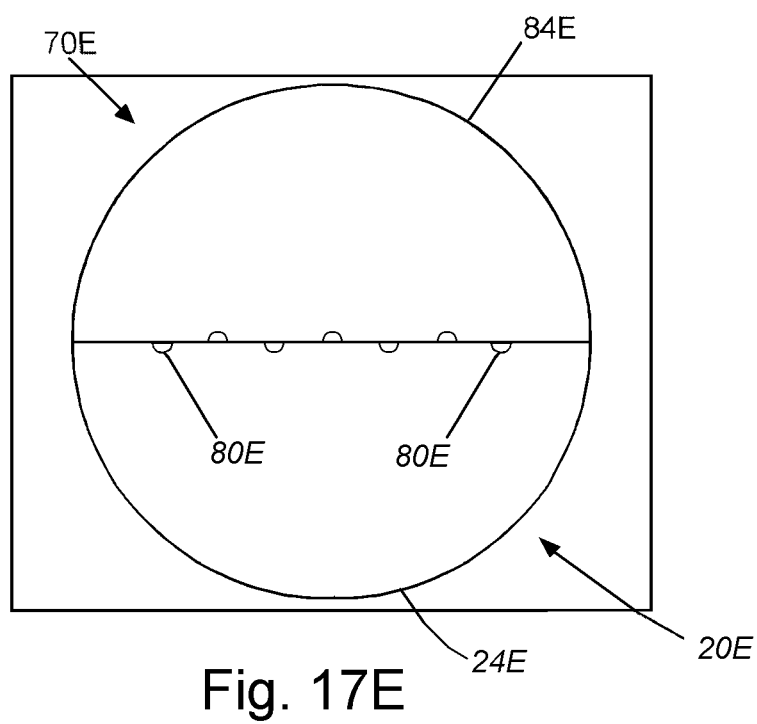

As a further alternate embodiment, FIG. 17E illustrates a flash chamber 20E having a plurality or multiplicity of small-cross-section channels 80E on each of opposing walls of the chamber (i.e. alternating semi-circular, semi-ovular or semi-polygonal surfaces). All channels 80E can be of similar, or approximately similar size, or various of the channels 80E can be of differing sizes. A benefit of this design is that since each channel 80E is a semi-circle only on one half of the flash chamber 20E (the two halves are the chamber portion 24E and cover 70E), capillary action is not dependent upon mating and bonding of the two halves and the quality of the seam therebetween. While the small channels 80E are shown as semi-circular in cross section, a variety of regular and irregular cross-sectional shapes are also contemplated according to further alternate embodiments.

Note that the overall size of the chamber flash is highly variable in various embodiments. In illustrative embodiments, the gap between confronting walls can, for example, be a constant or varying dimension of between approximately 0.5 mm-3.0 mm. The other dimensions of the chamber can be appropriate scaled in view of this gap, either based upon the dimensions of the Figures, or base upon other factors, such as ease of viewing by an operator. However, the illustrative gap dimension is illustrative of a wide range of possible dimensions depending upon the underlying geometry of the chamber, the characteristics of the blood to be viewed therein, and other appropriate factors.

FIGS. 18A-18C, 19A-19C, 20A-20C, 21A-21D, and 22A-22B are various schematic perspective and cross-sectional illustrations of a plurality of illustrative embodiments of the above-described flash chamber 20 and a general procedure for assembling such a flash chamber from individual components thereof. Again, like reference numbers to those provided above for the components of the generalized flash chamber 20 are used to describe structurally and functionally similar components in each embodiment, with the addition of an appropriate, respective suffix (a-e).

Figure 18A:
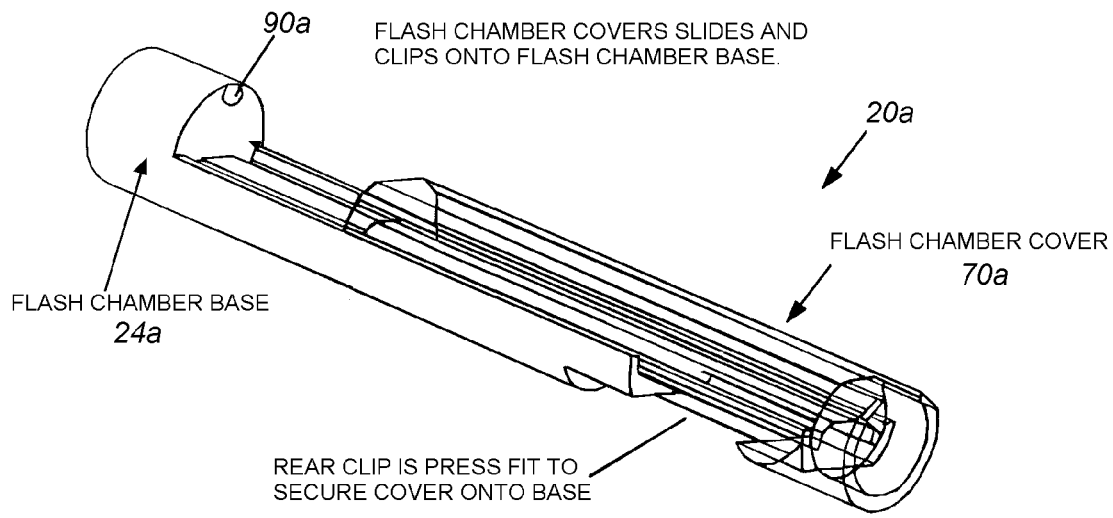
FIGS. 18A-18C are schematic illustrations of individual components of an illustrative flash chamber and a procedure for assembling the same.
Figure 18B:
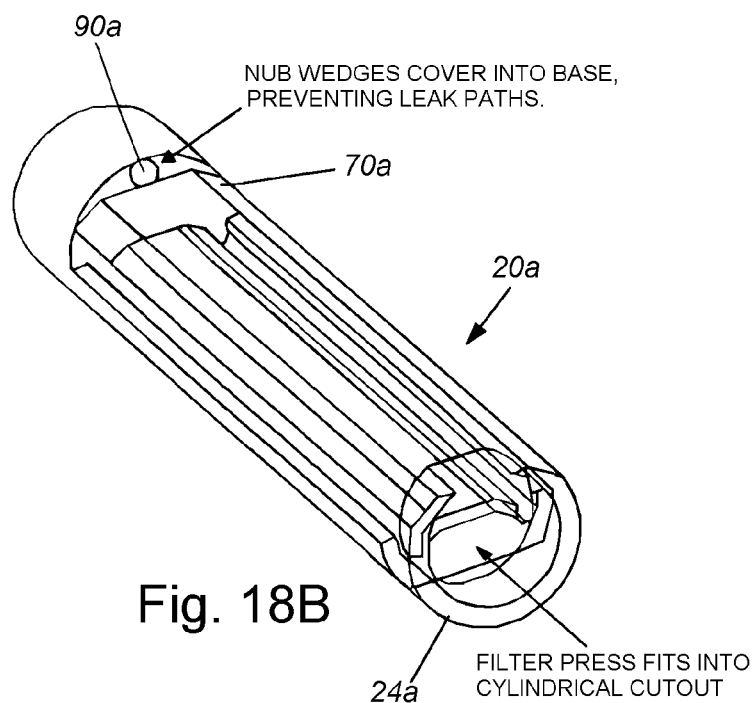
Figure 18C:
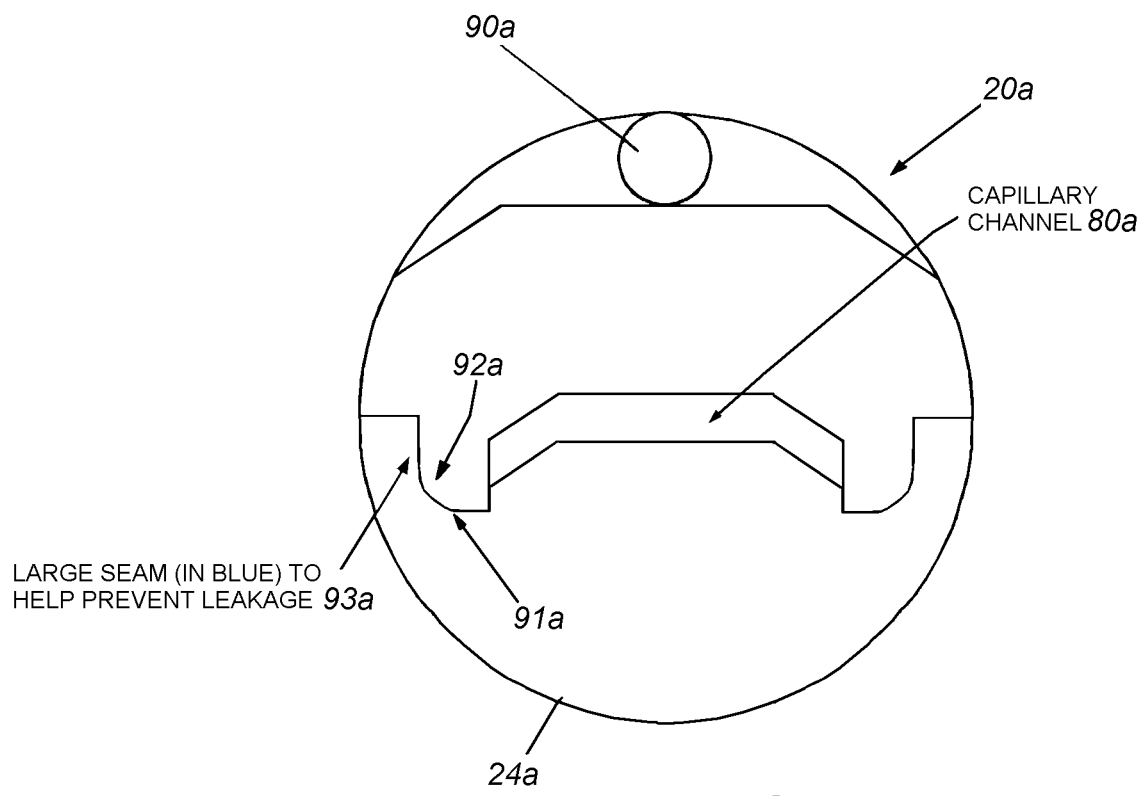

With Reference to the embodiment of FIGS. 18A-18C, the illustrative flash chamber 20 includes a chamber portion 24$a$ (or base) and cover 70$a$. The chamber portion 24$a$ includes a nub or raised projection feature 90$a$ that traps/wedges the cover 70$a$ to the chamber portion 24$a$ when assembled (referring to FIGS. 18B and 18C). The combination of the chamber portion 24$a$ (or base) and cover 70$a$ forms (between confronting walls thereof) the capillary channel 80$a$ (see cross section view, FIG. 18C). The chamber portion 24 (or base) defines a curved surface 91$a$ that mates with the complementary curved surface 92$a$ of the cover 70$a$ to create a circuitous seam/path 93 to help prevent leakage. It should be clear that the shape of the path is variable in alternate embodiments. More or fewer undulating features can be included and their shapes can be varied. For example, a variety of linear and/or curvilinear cross section shapes can be defined. Also, in any of the embodiments herein, the various components can be formed using a variety of techniques (e.g. extruding, molding, etc.) using similar or dissimilar materials (i.e. a transparent and an opaque material).

Figure 19A:
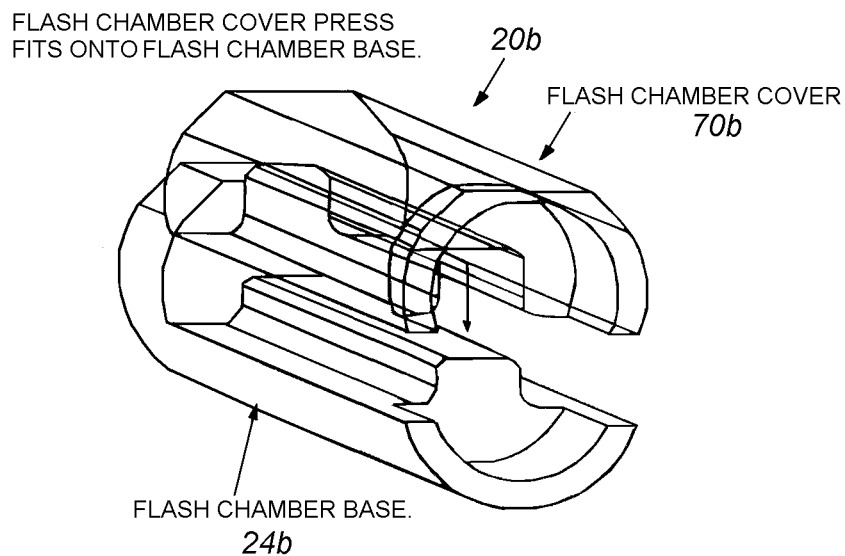
FIGS. 19A-19C are schematic illustrations of individual components of another illustrative flash chamber and a procedure for assembling the same.
Figure 19B:
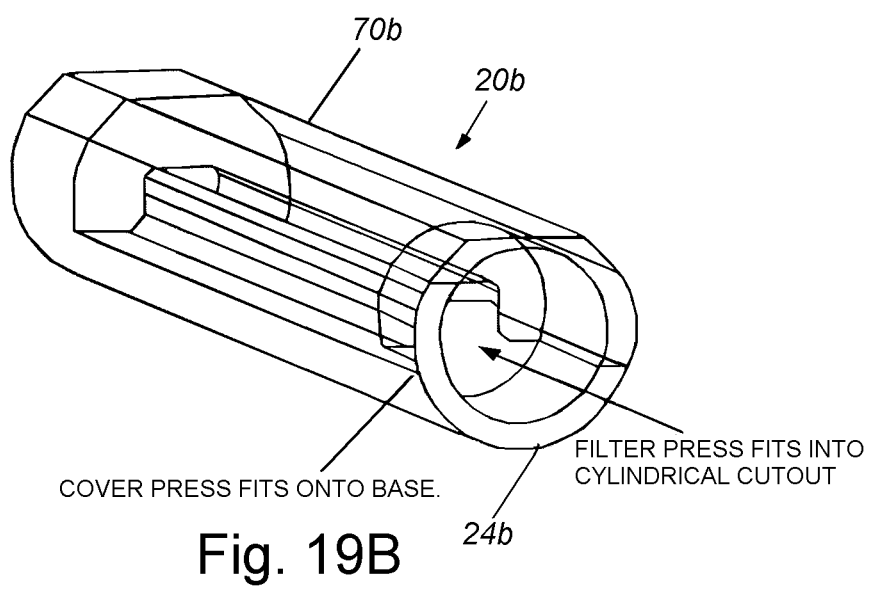
Figure 19C:
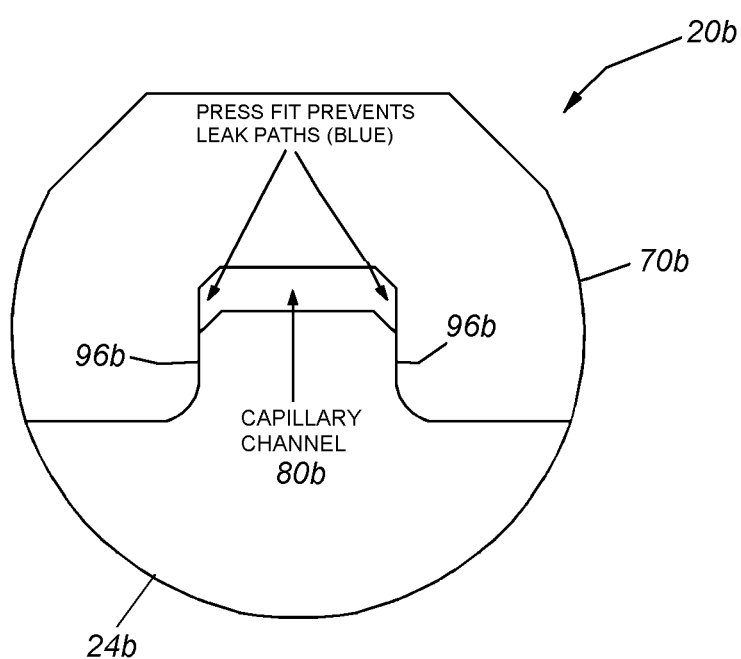

With reference now to another embodiment, shown in FIGS. 19A-19C the flash chamber 20$b$ includes a chamber portion 24$b$ (or base) and cover 70$b$. The cover 70$b$ press fits onto the chamber portion 24$b$ at locations 96$b$ when assembled (referring to FIGS. 19B and 19C). The respective confronting walls in the combination of the chamber portion 24$b$ (or base) and cover 70$b$ forms the capillary channel 80$b$ (see cross section view, FIG. 19C). Like other embodiments described herein, the particular geometry of the interengaging surfaces on each component can be varied for (for example) sealing and/or manufacturing purposes.

Figure 20A:
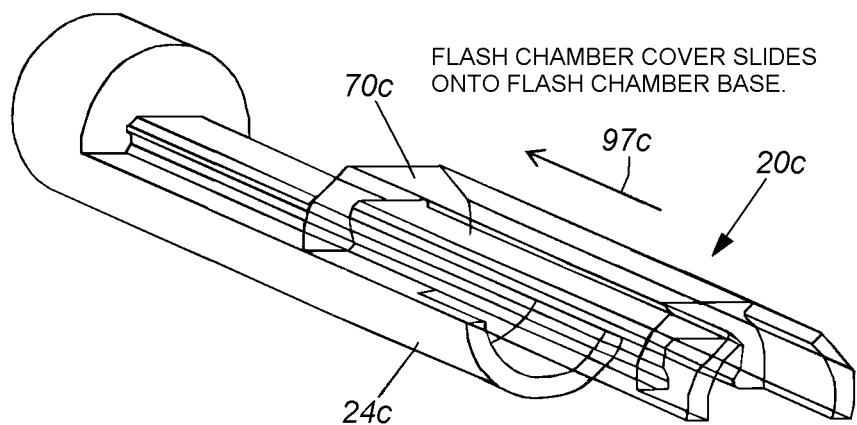
FIGS. 20A-20C are schematic illustrations of individual components of another illustrative flash chamber and a procedure for assembling the same.
Figure 20B:
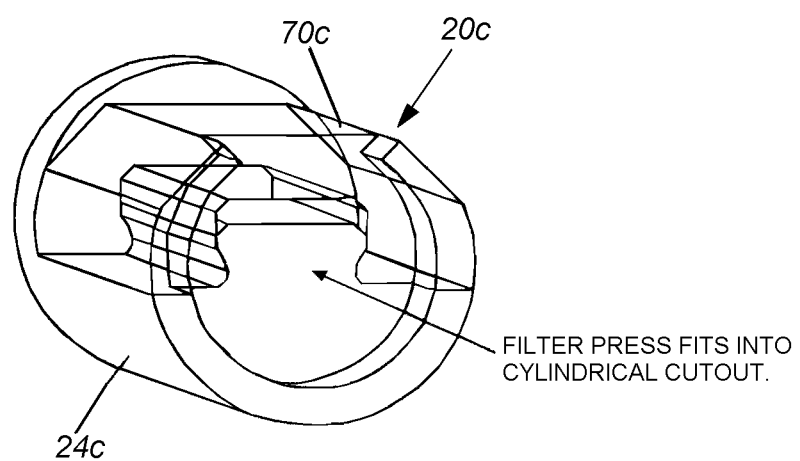
Figure 20C:
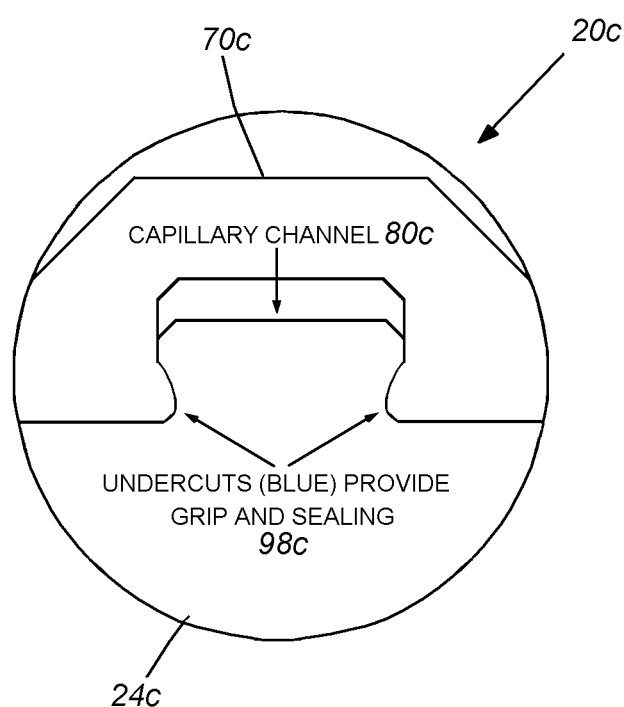
Figure 21A:
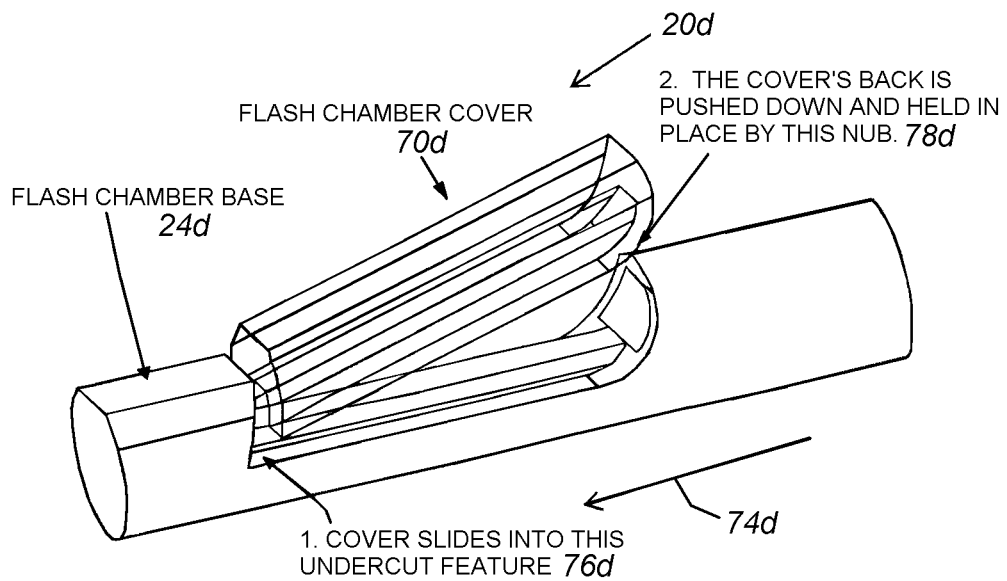
FIGS. 21A-21D are schematic illustrations of individual components of another illustrative flash chamber and a procedure for assembling the same.
Figure 21B:
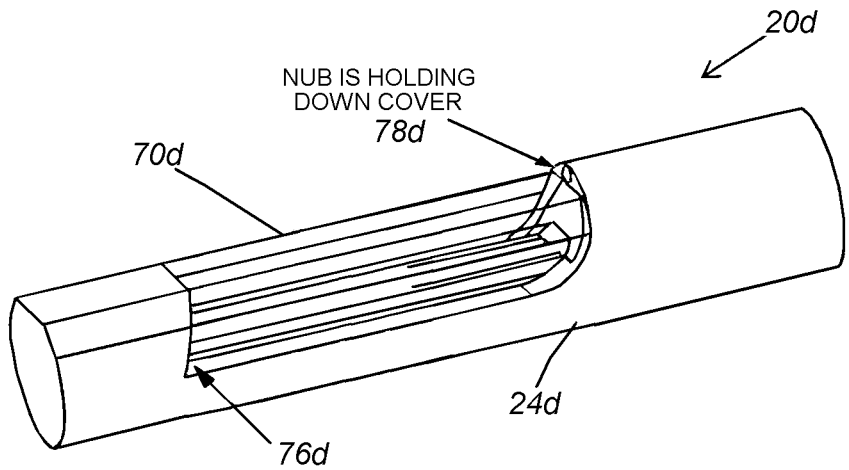
Figure 21C:
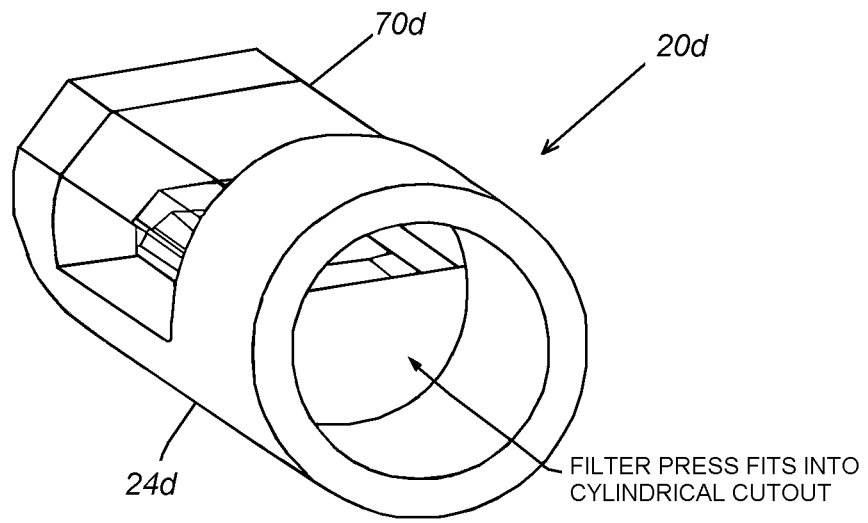
Figure 21D:
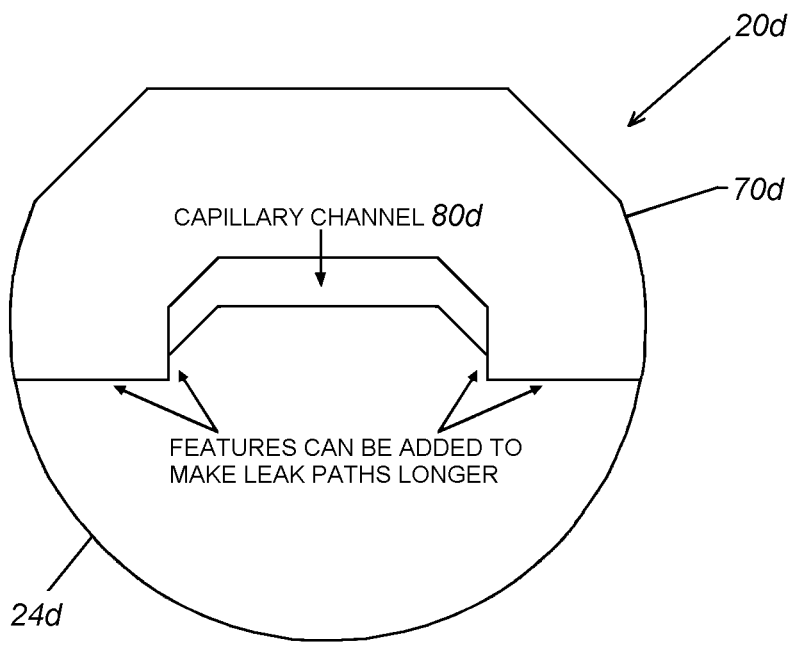

With reference now to the embodiment of FIGS. 20A-20C the flash chamber 20$c$ includes a chamber portion 24$c$ (or base) and cover 70$c$. The cover 70$c$ slides onto the chamber portion 24$c$ along direction 97$c$ in order to effect assembly of the chamber 20$c$. The cover 70$c$ and chamber portion 24$c$ include undercuts 98$c$ that function to make the cover grip onto the chamber portion to seal the flash chamber 20$c$ when assembled (referring to FIGS. 20B and 20C). The undercuts 98$c$ are configured to provide an interference fit between the assembled components so as to prevent the cover 70$c$ from sliding backwards during use. The combination of the chamber portion 24$c$ (or base) and cover 70$c$ forms the capillary channel 80$c$ (see cross section view, FIG. 20C). The size and geometry of the undercut portion (among others can be varied. Likewise, multiple undercuts arranged (for example) in parallel can be provided in alternate embodiments to enhance sealing and fitment.

With reference now to the embodiment of FIGS. 21A-21D the flash chamber 20$d$ includes a chamber portion 24$d$ (or base) and cover 70$d$. The cover 70$d$ slides onto the chamber portion 24$d$ along direction along direction 74$d$ into an undercut feature of the chamber portion 76$d$. The chamber portion 24$d$ includes a nub or raised projection feature 78$d$ that traps/ wedges the cover 70d to the chamber portion 24d when assembled (referring to FIGS. 21B and 21C). The confronting walls in the combination of the chamber portion 24d (or base) and cover 70d forms the capillary channel 80d (see cross section view, FIG. 21D). Note that the nub described herein can be substituted fro a detent, with an associated raised projection on the other, confronting component. In general, the two components of the flash chamber portion can be joined by such "interengaging formations" that enable secure alignment and locking of the components. Moreover, a variety of other interengaging formations can be substituted in further alternate embodiments.

Figure 22A:
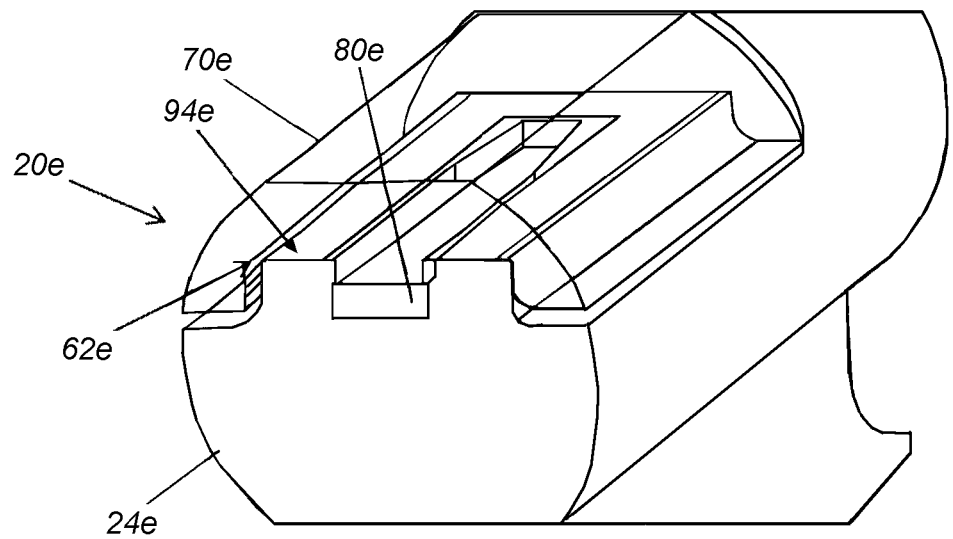
FIGS. 22A and 22B are schematic illustrations of individual components of yet another illustrative flash chamber and a procedure for assembling the same.
Figure 22B:
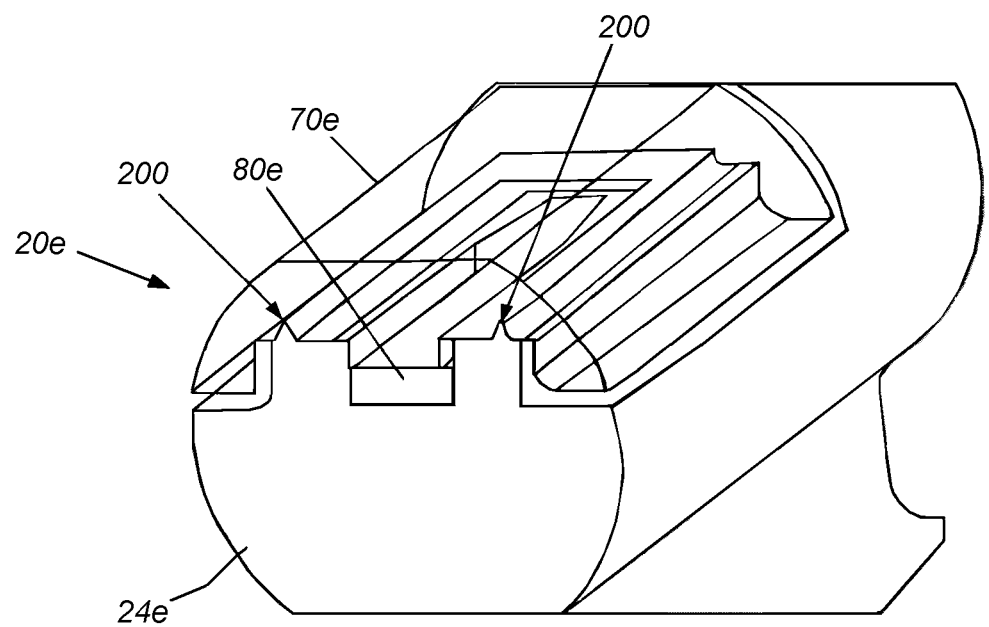

Reference is now made to yet another embodiment of the flash chamber 20e, as shown in FIGS. 22A and 22B. Referring to FIG. 22A, the flash chamber 20e includes a chamber portion 24e and a cover 70e. The cover 70e is positioned over the chamber portion 24e. An inner surface 62e of the cover 70e is bonded or adhered to a raised portion 94e of the chamber portion 24e to create capillary channel 80e using, for example, an material-appropriate adhesive applied to the raised portion 94e prior to assembly. In some embodiments, the cover portion 70e and the chamber portion 24e are fabricated using a plastic material and a solvent is applied to the inner surface 62e and raised portion 94e to cause the cover portion 70e to bond to the chamber portion 24e.

Referring to FIG. 22B, the flash chamber 20e again includes a chamber portion 24e and a cover 70e. Ultrasonic welding is used to couple the cover 70e to the chamber portion 24e. In ultrasonic welding, a high frequency (e.g., 15 kHz to 40 kHz) low-amplitude vibration is used to create heat between to materials to be joined. Heat is created by creating friction between the two materials. The interface of the two parts is specially designed to concentrate the energy for welding the two parts together to create capillary channel 80e. In this embodiment, a "v" shaped energy director 200 is formed on the chamber portion 24e to concentrate the energy applied along the edge of the energy director during ultrasonic welding. The "v" shaped energy director can be located on either the chamber portion or the cover 70e. Note that another welding technique or a light-based bonding technique (e.g. UV cured adhesive, laser welding, etc.) can be substituted in this and other embodiments. Appropriate fixtures and assemblies can be provided to facilitate the use of such techniques in a manner clear to those of ordinary skill.

Figure 23:
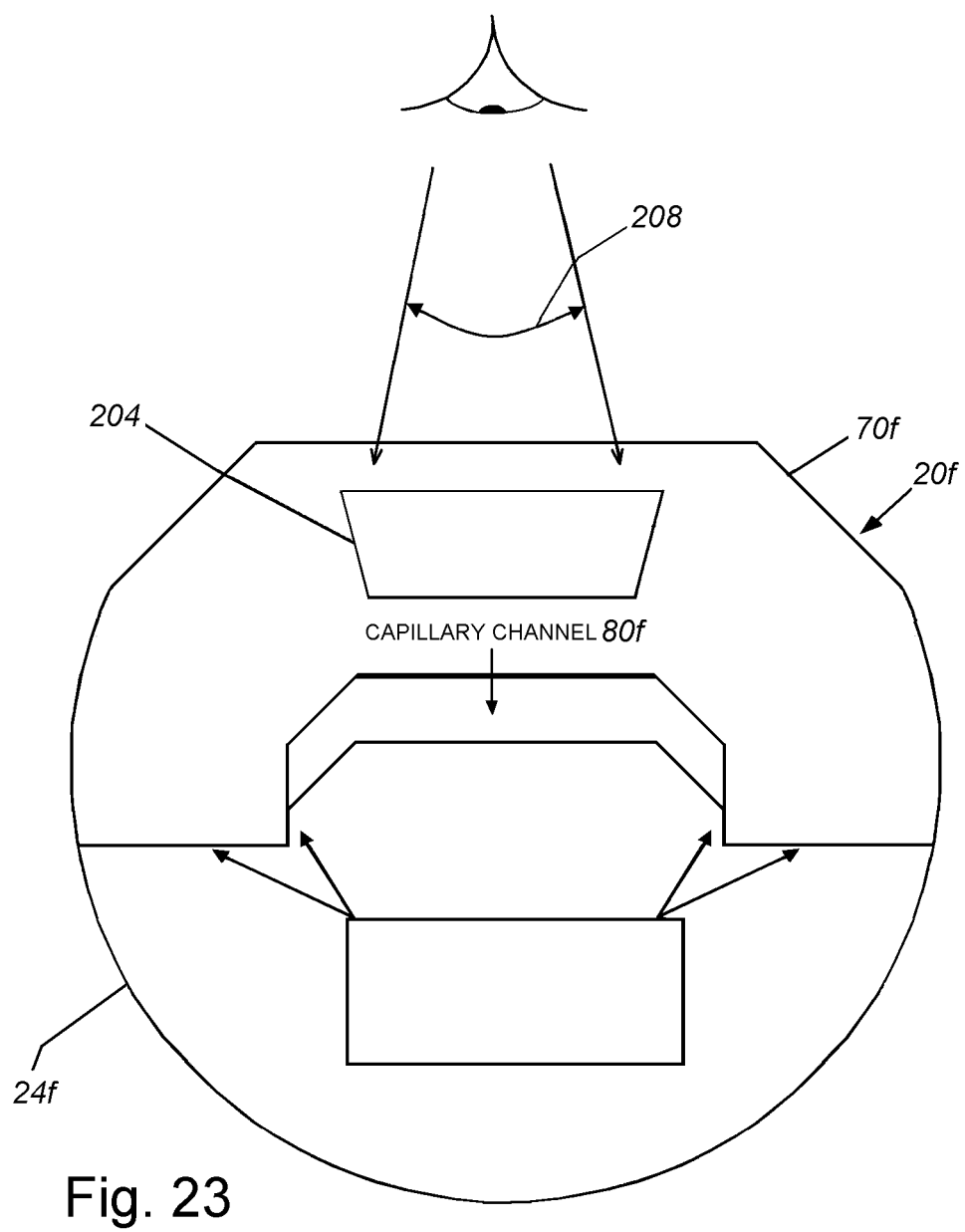
FIG. 23 is a schematic, cross-sectional illustration of a flash chamber that includes a lens element, according to an illustrative embodiment.

FIG. 23 is a schematic illustration of a flash chamber 20f that includes a lens element 204, according to an illustrative embodiment. Again, structurally and functionally similar components to those described for the generalized flash chamber 20 above are provided with like reference numbers including the suffix (f). The lens element 204 improves the visibility for the user of the contents of the capillary channel 80f by both magnifying the contents of the capillary channel 80f and improving the viewing angle 208 (e.g., from above) for the user. A small amount of blood in the capillary channel 80f will appear larger in size than it is due to the lens' magnification effect. In addition, a small sized capillary channel 80f can be used which may substantially increase the speed of blood filling the capillary channel 80f and reduce the amount of blood required to be drawn before inserting the catheter into the blood vessel. In addition, the lens element 204 can be constructed and arranged to increase the viewing angle over which a user may be able to view the contents of the capillary channel 80f. In some embodiments, the lens element 204 is a separate component that is inserted into a corresponding receptacle or region of the cover 70f. In some embodiments, the lens element 204 is a feature formed in the cover 70f during fabrication of the cover 70f.

The foregoing has been a detailed description of illustrative embodiments of the invention. Various modifications and additions can be made without departing from the spirit and scope of this invention. Each of the various embodiments described above can be combined with other described embodiments in order to provide a wide variety of combinations of illustrative features. Furthermore, while the foregoing describes a number of separate embodiments of the apparatus and method of the present invention, what has been described herein is merely illustrative of the application of the principles of the present invention. For example, it is expressly contemplated that a variety of bonding and/or joining techniques can be employed or combined to assemble components herein. Likewise, the additional accessories can be provided to the system described herein in order to increase its utility for an operator. Additionally, while components of the overall assembly and individual features are shown with a particular scale, such can be varied in size and scale to accommodate human or animal patients of a differing size or physiology—such as pediatric patients. Accordingly, this description is meant to be taken only by way of example, and not to otherwise limit the scope of this invention.

What is claimed is:

1. A catheter and insertion needle assembly, comprising an insertion needle;
a catheter forming a sleeve that overlies at least a portion of the insertion needle;
a housing coupled to the insertion needle and the catheter, the insertion needle and catheter being slidably mounted to the housing to permit movement of the insertion needle relative to the catheter, and to permit approximately coaxial movement of the insertion needle and the catheter relative to the housing, wherein the housing comprises a chamber having a capillary channel for more quickly receiving blood from a subject; and
a separate transparent cover, and wherein the capillary channel is disposed between one and other confronting respective walls of the transparent cover and the chamber;
said confronting walls engaged together in a sealed relationship;
said cover comprising a transparent or translucent top portion that affords a wide range of viewing angles;
said housing comprising a housing portion having an outer wall;
the capillary channel comprising at least one capillary passage disposed between the housing portion outer wall defining the one of the confronting walls and the cover top portion defining the other of the confronting walls.

2. The catheter and insertion needle assembly as set forth in claim 1 wherein the housing includes a slider that enables the insertion needle and the catheter to slide relative to each other between a position in which the catheter is remote from a tip of the insertion needle and a position in which the catheter covers the insertion needle.

3. The catheter and insertion needle assembly as set forth in claim 2 wherein the slider includes a slider lock that is constructed and arranged to provide at least one of a tactile and an audible click when the catheter covers the tip.

4. The catheter and insertion needle assembly as set forth in claim 1 including a sealing element in the capillary passage.

5. The catheter and insertion needle assembly as set forth in claim 1 wherein the confronting walls define one of (a) confronting polygonal surfaces, (b) alternating semicircular surfaces, (c) confronting concentric, spaced-apart semicircular surfaces (d) confronting planar surfaces (e) confronting non-concentric, semi-circular surfaces.

6. The catheter and insertion needle assembly as set forth in claim 1 wherein the transparent cover is attached to the chamber by interengaging formations.

7. The catheter and insertion needle assembly as set forth in claim 1 wherein the insertion needle comprises
- a needle shaft and a needle tip extending distally from a proximal shaft junction, the needle tip defining a distal-most sharp point,
- a side port in fluid communication with a lumen of the needle shaft located on a first side adjacent to the shaft junction, and
- an upwardly curved heel on the needle tip along a second side opposite the first side that extends from the junction to the distal-most sharp point and thereby locates the point adjacent to a longitudinal axis of the shaft.

8. The catheter and insertion needle assembly as set forth in claim 7 wherein the needle tip interconnects with a straight, cylindrical shaft section having the catheter at a relatively circular interface junction.

9. The catheter and insertion needle assembly as set forth in claim 8 wherein the circular junction resides in a plane that is approximately perpendicular to the longitudinal (axis of elongation) taken along a center of the shaft.

10. The catheter and insertion needle assembly as set forth in claim 1 wherein the transparent cover is semi-circular in shape in order to afford a wide range of viewing angles from above.

11. The catheter and insertion needle assembly as set forth in claim 1 wherein the confronting walls are constructed and arranged to provide a varying thickness of the capillary channel between the transparent cover and the chamber.

12. The catheter and insertion needle assembly as set forth in claim 1 wherein the confronting walls are planar and are oriented at a non-parallel angle with respect to each other.

13. The catheter and insertion needle assembly as set forth in claim 1 wherein the confronting walls are defined by a pair of spaced-apart confronting walls, each having a continuous planar shape so as to define a substantially constant-spacing/width region.

14. The catheter and insertion needle assembly as set forth in claim 1 wherein said housing portion outer wall includes a peripheral outer portion and a raised portion.

15. The catheter and insertion needle assembly as set forth in claim 14 wherein the raised portion has a height measured from a base of the outer wall that is greater than the height of the peripheral portion.

16. The catheter and insertion needle assembly as set forth in claim 15 wherein the cover top portion includes a recess that mates with the raised portion and that defines the capillary passage between the raised portion and the recess.

17. The catheter and insertion needle assembly as set forth in claim 16 wherein the cover top portion has, at opposite ends of the capillary passage, a curved surface that mates with a complementary curved surface of the housing portion.

18. The catheter and insertion needle assembly as set forth in claim 16 wherein the confronting walls are defined by a series of semi-circular channels.

19. The catheter and insertion needle assembly as set forth in claim 1 wherein one of the cover and housing defines a raised portion and the other of the cover and housing defines a complementary recess.

20. The catheter and insertion needle assembly as set forth in claim 19 wherein said housing portion outer wall includes a peripheral outer portion and a raised portion, the cover top portion includes the recess that mates with the raised portion and that defines the capillary passage between the raised portion and the recess, and wherein the cover top portion is semi-circular in order to afford the wide range of viewing angles.

\* \* \* \* \*